US008785686B2

(12) United States Patent
Barnicki et al.

(10) Patent No.: US 8,785,686 B2
(45) Date of Patent: Jul. 22, 2014

(54) PROCESS FOR RECOVERING AND RECYCLING AN ACID CATALYST

(75) Inventors: Scott Donald Barnicki, Kingsport, TN (US); Stephen Neal Falling, Kingsport, TN (US); Jeffrey Scott Kanel, Kingsport, TN (US); Robert Sterling Kline, Kingsport, TN (US); Peter Borden Mackenzie, Kingsport, TN (US); Andrew James Vetter, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 175 days.

(21) Appl. No.: 13/431,335

(22) Filed: Mar. 27, 2012

(65) Prior Publication Data
US 2012/0215027 A1 Aug. 23, 2012

Related U.S. Application Data

(63) Continuation-in-part of application No. 12/889,045, filed on Sep. 23, 2010.

(51) Int. Cl.
*C07C 59/06* (2006.01)
*C07C 51/48* (2006.01)

(52) U.S. Cl.
USPC .......................................... 562/579; 562/580

(58) Field of Classification Search
CPC ................................ C07C 59/06; C07C 51/48
See application file for complete search history.

(56) References Cited

U.S. PATENT DOCUMENTS

| | | | |
|---|---|---|---|
| 2,152,852 A | 4/1939 | Loder | |
| 2,153,064 A | 4/1939 | Larson | |
| 2,211,624 A | 8/1940 | Loder et al. | |
| 2,211,625 A | 8/1940 | Loder | |
| 2,298,138 A | 10/1942 | Loder | |
| 2,436,209 A | 2/1948 | Elgin | |
| 2,443,482 A | 6/1948 | Shattuck | |
| 3,333,924 A | 8/1967 | Hazen et al. | |
| 3,751,453 A | 8/1973 | Kurkov et al. | |
| 3,754,028 A | 8/1973 | Lapporte et al. | |
| 3,801,627 A | 4/1974 | Kurkov et al. | |
| 3,859,349 A | 1/1975 | Cody | |
| 3,911,003 A | 10/1975 | Suzuki | |
| 3,927,078 A | 12/1975 | Lapporte et al. | |
| 3,948,977 A | 4/1976 | Suzuki | |
| 3,948,986 A | 4/1976 | Suzuki | |
| 4,016,208 A | 4/1977 | Suzuki | |
| 4,052,452 A | 10/1977 | Scardigno et al. | |
| 4,087,470 A | 5/1978 | Suzuki | |
| 4,112,245 A | 9/1978 | Zehner et al. | |
| 4,128,575 A | 12/1978 | Leupold et al. | |
| 4,136,112 A | 1/1979 | Bakshi | |
| 4,140,866 A | 2/1979 | Nielsen | |
| 4,153,809 A | 5/1979 | Suzuki | |
| 4,228,305 A | 10/1980 | Suzuki | |
| 4,275,234 A | 6/1981 | Baniel et al. | |
| 4,291,007 A | 9/1981 | Baniel | |
| 4,308,397 A | 12/1981 | Suzuki | |
| 4,366,333 A | 12/1982 | Wilkes | |
| 4,409,395 A | 10/1983 | Miyazaki et al. | |
| 4,431,486 A | 2/1984 | Balmat | |
| 4,440,734 A | 4/1984 | Kougioumoutzakis | |
| 4,501,917 A | 2/1985 | Schmidt et al. | |
| 4,691,048 A | 9/1987 | Hugues et al. | |
| 4,824,997 A | 4/1989 | Macfarlane et al. | |
| 4,935,102 A | 6/1990 | Berg | |
| 4,966,658 A | 10/1990 | Berg | |
| 4,990,629 A | 2/1991 | Souma | |
| 5,026,927 A | 6/1991 | Andrews et al. | |
| 5,210,335 A | 5/1993 | Schuster et al. | |
| 5,214,219 A | 5/1993 | Casale et al. | |
| 5,276,181 A | 1/1994 | Casale et al. | |
| 5,423,955 A | 6/1995 | Berg | |
| 5,455,372 A | 10/1995 | Hirai et al. | |
| 5,723,662 A | 3/1998 | Ebmeyer et al. | |
| 5,932,772 A | 8/1999 | Argyropoulos et al. | |

(Continued)

FOREIGN PATENT DOCUMENTS

| | | |
|---|---|---|
| DE | 3133353 C2 | 3/1983 |
| EP | 0 114 657 B1 | 3/1987 |
| EP | 0 676 239 A2 | 10/1995 |
| EP | 1 679 331 A1 | 7/2006 |
| GB | 508383 A | 6/1939 |
| GB | 1499245 A | 1/1978 |
| GB | 2179337 A | 7/1986 |
| IL | 89044 A | 3/1993 |
| IL | 89044 A * | 3/1994 |
| JP | 56100741 A | 8/1981 |

(Continued)

OTHER PUBLICATIONS

Bonrath et al, Sustainability, Methantrisulfonic Acid: A Highly Efficient Strongly Acidic Catalyst for Wagner-Meerwein Rearrangement, Friedel-Crafts Alkylation and Acylation Reactions. Examples from Vitamin E Synthesis, 2009, 1, pp. 161-168.*
Baniel, A., et al., "Acid-Base Couple Solvents in Recovery of Mineral Acids From Waste Streams", Proceedings of 2nd International Conference on Separations Science and Technology, Oct. 1-4, 1989, pp. 667-674.

(Continued)

*Primary Examiner* — Paul A Zucker
(74) *Attorney, Agent, or Firm* — Jennifer R. Knight; Eric Middlemas

(57) ABSTRACT

Disclosed is a process for the extractive recovery of an acid catalyst from an aqueous mixture of glycolic acid with an extraction solvent comprising a tertiary amine or an onium carboxylate compound, a modifier, and a diluent. The acid catalyst, which can comprise strong acids such as sulfuric acid, alkyl sulfonic acids, and fluoroalkyl sulfonic acids, can be recovered by back extraction with aqueous formaldehyde and recycled to a process for the preparation of glycolic acid by the acid-catalyzed carbonylation of formaldehyde. Also disclosed is a process for the preparation of glycolic acid by the acid-catalyzed hydrocarboxylation of formaldehyde.

19 Claims, No Drawings

(56) References Cited

U.S. PATENT DOCUMENTS

| | | | |
|---|---|---|---|
| 5,952,530 A | 9/1999 | Argyropoulos et al. | |
| 6,252,121 B1 | 6/2001 | Argyropoulos et al. | |
| 6,291,725 B1 | 9/2001 | Chopade et al. | |
| 6,294,700 B1 | 9/2001 | Kanel et al. | |
| 6,303,829 B1 | 10/2001 | Kanel et al. | |
| 6,307,108 B1 | 10/2001 | Argyropoulos et al. | |
| 6,307,109 B1 | 10/2001 | Kanel et al. | |
| 6,307,110 B1 | 10/2001 | Argyropoulos et al. | |
| 6,310,260 B1 | 10/2001 | Argyropoulos et al. | |
| 6,376,723 B2 * | 4/2002 | Drent et al. | 568/864 |
| 7,122,698 B2 | 10/2006 | Yoshida et al. | |
| 7,164,040 B2 | 1/2007 | Kuroda et al. | |
| 7,223,885 B2 | 5/2007 | Van Krieken | |
| 7,439,391 B2 | 10/2008 | Gallagher et al. | |
| 7,615,671 B2 | 11/2009 | Puckette et al. | |
| 7,709,689 B2 | 5/2010 | Kilner et al. | |
| 7,772,423 B2 | 8/2010 | Celik et al. | |
| 8,466,328 B2 | 6/2013 | Barnicki et al. | |
| 2004/0222153 A1 | 11/2004 | Baniel et al. | |
| 2006/0160197 A1 | 7/2006 | Li et al. | |
| 2007/0123739 A1 | 5/2007 | Crabtree et al. | |
| 2008/0275277 A1 | 11/2008 | Kalagias | |
| 2009/0143612 A1 | 6/2009 | Puckette et al. | |
| 2011/0144388 A1 | 6/2011 | Sun et al. | |
| 2011/0166383 A1 | 7/2011 | Sun et al. | |
| 2012/0046481 A1 | 2/2012 | Barnicki et al. | |
| 2012/0046500 A1 | 2/2012 | Barnicki et al. | |
| 2012/0078010 A1 | 3/2012 | Barnicki et al. | |

FOREIGN PATENT DOCUMENTS

| | | |
|---|---|---|
| JP | 56131546 A | 10/1981 |
| JP | 56133237 A | 10/1981 |
| JP | 5746934 A | 3/1982 |
| JP | 57040442 A | 3/1982 |
| JP | 57102837 A | 6/1982 |
| JP | 6228045 A | 8/1994 |
| JP | 1999147042 A | 6/1999 |
| JP | 2004131411 A | 4/2004 |
| RU | 1436453 A1 | 9/1996 |
| WO | WO 97/15543 A1 | 5/1997 |
| WO | WO 2006/069127 A1 | 6/2006 |
| WO | WO 2009/140850 A1 | 11/2009 |
| WO | WO 2012/040007 A2 | 3/2012 |
| WO | WO 2012/130316 A1 | 10/2012 |

OTHER PUBLICATIONS

Hou-Yong, Sun, et al. "Reactive extraction of glycolic acid in high content solution with tri-n-octylamine" Journal of Chemical Engineering of Chinese Universities, Feb. 2007, vol. 21 pp. 26-30.

USPTO Office Action for U.S. Appl. No. 13/431,358 dated Nov. 12, 2013.

Notification of Transmittal of the International Search Report and the Written Opinion of the International Search Authority with Mail Date of Mar. 15, 2012 for International Application No. PCT/US2011/051490.

Notification of Transmittal of the International Search Report and the Written Opinion of the International Search Authority with Mail Date of Nov. 28, 2011 for International Application No. PCT/US2011/047842.

Celik et al., "Synthesis of precursors to ethylene glycol from formaldehyde and methyl formate catalyzed by heteropoly acids", Journal of Molecular Catalysis A: Chemical 288, (2008), pp. 87-96.

Celik et al., "Vapor-phase carbonylation of dimethoxymethane of H-Faujasite", Angewandte. Chemie Int. Ed. 2009, 48, pp. 4813-4815.

Asci, Yavuz Selim et al. "Extraction of Glycolic Acid from Aqueous Solutions by Amberlite La-2 in Difference Diluent Solvents" J. Chem Eng. Data 2009, 54, 2791-2794.

Bizek, Vladislav et al. "Amine Extraction of Hydroxycarboxylic Acids. 1. Extraction of Citric Acid with 1-Octanol/n-Heptane Solutions of Trialkylamine" Ind. Eng. Chem. Res. 1992, 31, 1554-1562.

Tamada, Janet A. et al. "Extraction of Carboxylic Acids with Amine Extractants. 1. Equilibria and Law of Mass Action Modeling" Ind. Eng. Chem. Res. 1990, 29, 1319-1326.

Smith, E. Lester, et al., "The Acid-Binding Properties of Long-Chain Aliphatic Amines", J.S.C.I., 67, Feb. 1948 pp. 48-51.

Walker, "Formaldehyde", ACS Monograph, Washington, DC., (1964), p. 95.

Eyal, A., et al. "Recovery and Concentration of Strong Mineral Acids from Dilute Solutions Through LLX III. A "Temperature Swing" Based Process", Solvent Extraction and Ion Exchange, 9 (2), pp. 223-236 (1991).

Eyal, A.M., et al. "Recovery and Concentration of Strong Mineral Acids from Dilute Soltions Through LLX. I: Review of Parameters for Adjusting Extractant Properties and Analysis of Process Options", Solvent Extraction and Ion Exchange, 9 (2), pp. 195-210 (1991).

Eyal, A.M., et al. "Recovery and Concentration of Strong Mineral Acids from Dilute Solutions Through LLX. II. Reversible Extraction with Branched-Chain Amines", Solvent Extraction and Ion Exchange, 9(2), pp. 211-222 (1991).

Eyal, Aharon, et al. "Extraction of Strong Mineral Acids by Organic Acid-Base Couples", Ind. Eng. Chem. Process Des. Dev., (1982), vol. 21, No. 2, pp. 334-337.

Handbook of Solvent Extraction, Krieger Publishing Company, Malabar, FL, 1991, pp. 275-501.

Treybal, Robert E. "Methods of Calculation II. Stagewise Contact, Multicomponent Systems", Liquid Extraction, $2^{nd}$ Edition, McGraw-Hill Book Company, New York. 1963, pp. 275-276.

Treybal, Robert E., Liquid Extraction, $2^{nd}$ Ed., McGraw-Hill Book Company, New York, NY, 1963, pp. 349-366.

Gerberich, H. Robert, et al., "Formaldehyde", Kirk-Othmer Encyclopedia of Chemical Technology, vol. 11, $4^{th}$ Edition, 1994, pp. 929-951.

Treybal, Robert E., Liquid Extraction, $2^{nd}$ Ed., McGraw Hill Book Company, 1963, pp. 248-252.

Lynch, Kathleen M., et al., "Improved Preparations of 3-Chloro-2(chloromethyl)-1-propene and 1,1-Dibromo-2,2-bis(chloromethyl)-cyclopropane: Intermediates in the Synthesis of [1.1.1]Propellane", J. Org. Chem, 60, (1995), pp. 4666-4668.

"Tray Design and Operation", Distillation Design, McGraw-Hill, New York (1992), Chapter 6, pp. 259-363.

"Packing Design and Operation", Distillation Design, McGraw-Hill, New York, (1992), Chapter 8, pp. 421-521.

Seader, J.D., Ph.D, et al., "Distillation", Perry's Handbook of Chemical Engineering, Section 13, $7^{th}$ Ed., McGraw-Hill Book Co. 1999.

Lee, Sang Young, et al., "Carbonylation of Formaldehyde over Ion Exchange Resin Catalysts. 1. Batch Reactor Studies", Ind. Eng. Chem. Res., 32, (1993), pp. 253-259.

Xu, Qiang, et al., "Preparation and Catalytic Application of Cationic Metal Carbonyls", Science and Technology in Catalysis, (2002), pp. 215-218.

Xu, Qiang, "Metal carbonyl cations: generation, characterization and catalytic application", Coordination Chemistry Reviews, 231, (2002), pp. 83-108.

Suzuki, S., et al., "Ethylene Glycol from Methanol and Synthesis Gas via Glycolic Acid", Catalytic Conversions of Synthesis Gas and Alcohols to Chemicals, (1984). pp. 221-247.

Wang, Zheng Bao, et al., Carbonylation of Formaldehyde with Carbon Monoxide over Cation-Exchange Resin Catalysts, Bull. Chem. Soc. Jpn., 72, (1999), pp. 1935-1940.

Sano, Tsunejo, et al., "Synthesis of 1,3-dioxolan-4-one from trioxane and carbon monoxide on HZSM-5 zeolite", Chem. Community, (1997), pp. 1827-1828.

Souma, Yoshie, "Carbonylation at Ambient Pressure in Strong Acids", Journal of Synthetic Organic Chemistry, vol. 41, No. 6, (1983), pp. 561-569.

Soma, Yoshie, et al., "Normal-Pressure CO Addition Reaction of Formaldehyde and Related Compounds on Copper Carbonyl Catalyst", Catalyst 23, (1981), pp. 48-50.

Li, Tao, et al., "Carbonylation of formaldehyde catalyzed by p-toluenesulfonic acid", Catalysis Today, 111, (2006), pp. 288-291.

(56) References Cited

OTHER PUBLICATIONS

Souma, Yoshie, et al., "Synthesis of tert.-Alkanoic acid catalyzed by $Cu(CO)^+_n$ and $Ag(CO)^+_2$ under atmospheric pressure", Catalysis Today, 36, (1997), pp. 91-97.
Hendriksen, Dan E., "Intermediates to Ethylene Glycol: Carbonylation of Formaldehyde Catalyzed by NAFION Solid Perfluorosulfonic Acid Resin", Prep. A.C.S. Div. Fuel Chem., 28, (1983), pp. 176-190.
Bhattacharyya, S.K., et al., "High-Pressure Synthesis of Glycolic Acid from Formaldehyde, Carbon Monoxide, and Water in Presence of Nickel, Cobalt, and Iron Catalysts", Advanced Catalysts, 9, (1957), pp. 625-635.
Wegescheiderr, Rud., et al., "Addition of Acid Anhydrides to Aldehydes and Ketones", Royal and Imperial University of Vienna, presented at the meeting of Nov. 4, 1909, pp. 1-47.
King, Walter D., et al. "The Acid-Catalyzed Reaction of Acetic Anhydride with Some Oxocanes", Journal of Applied Polymer Science, vol. 18, (1974) pp. 547-554.
He, Dehua, et al., "Condensation of formaldehyde and methyl formate to methyl glycolate and methyl methoxy acetate using heteropolyacids and their salts", Catalysis Today, 51, (1999), pp. 127-134.
Co-pending U.S. Appl. No. 12/889,045, filed Sep. 23, 2010, Scott Donald Barnicki, et al.
Co-pending U.S. Appl. No. 12/889,065, filed Sep. 23, 2010 Scott Donald Barnicki, et al.
Co-pending U.S. Appl. No. 13/208,399, filed Aug. 12, 2011, Scott Donald Barnicki, et al.
Co-pending U.S. Appl. No. 13/431,308, filed Mar. 27, 2012, Scott Donald Barnicki, et al.
Co-pending U.S. Appl. No. 13/431,358, filed on Mar. 27, 2012, Scott Donald Barnicki, et al.
Co-pending U.S. Appl. No. 13/431,369, filed Mar. 27, 2012, Scott Donald Barnicki, et al.
Co-pending U.S. Appl. No. 13/431,402, filed Mar. 27, 2012, Scott Donald Barnicki, et al.
Co-pending U.S. Appl. No. 13/431,386, filed Mar. 27, 2012, Scott Donald Barnicki, et al.
Co-pending U.S. Appl. No. 13/491,954, filed Jun. 8, 2012 Mesfin Ejerssa Janka.
USPTO Notice of Allowance for U.S. Appl. No. 12/889,045 dated Jul. 18, 2012.
Notification of Transmittal of the International Search Report and the Written Opinion of the International Search Authority with Mail Date of Aug. 13, 2013 for International Application No. PCT/US2013/033458.
Notification of Transmittal of the International Search Report and the Written Opinion of the International Search Authority with Mail Date of Jun. 25, 2013 for International Application No. PCT/US2013/033501.
Notification of Transmittal of the International Search Report and the Written Opinion of the International Search Authority with Mail Date of Aug. 16, 2013 for International Application No. PCT/US2013/033410.
Notification of Transmittal of the International Search Report and the Written Opinion of the International Search Authority with Mail Date of Jun. 21, 2013 for International Application No. PCT/US2013/033520.
Notification of Transmittal of the International Search Report and the Written Opinion of the International Search Authority with Mail Date of Jun. 21, 2013 for International Application No. PCT/US2013/033411.
Notification of Transmittal of the International Search Report and the Written Opinion of the International Search Authority with Mail Date of Jul. 8, 2013 for International Application No. PCT/US2013/033494.
Notification of Transmittal of the International Search Report and the Written Opinion of the International Search Authority with Mail Date of Jul. 12, 2013 for International Application No. PCT/US2013/033446.
Co-pending U.S. Appl. No. 13/896,706, filed May 17, 2013, Scott Donald Barnicki, et al.
USPTO Notice of Allowance for U.S. Appl. No. 12/889,065 dated Oct. 15, 2012.
Malinowski, J. J. "Evaluation of Liquid Extraction Potentials for Downstream Separation of 1,3-Propanediol", Biotechnology Techniques, vol. 18, No. 2 (Jan. 1, 1999), pp. 127-130.
Cox et al. "Mechanistic Studies in Strong Acids . . . ", Journal of Organic Chemistry, vol. 51, No. 19 (Sep. 1, 1986), pp. 3619-3624.
Li et al. "Aqueous Two-phase Extraction of 1,3-propanediol from Glycerol-based Fermentation Broths", Separation and Purification Technology Separation and Purification Technology, vol. 66, No. 3 (May 7, 2009), pp. 472-478.
USPTO Office Action dated Jul. 18, 2013 for U.S. Appl. No. 13/431,386.
USPTO Notice of Allowance for U.S. Appl. No. 13/431,358 dated Aug. 2, 2013.
USPTO Notice of Allowance for U.S. Appl. No. 12/889,045 dated Sep. 19, 2013.
USPTO Notice of Allowance for U.S. Appl. No. 13/896,706 dated Oct. 4, 2013.

\* cited by examiner

PROCESS FOR RECOVERING AND RECYCLING AN ACID CATALYST

CROSS REFERENCE TO RELATED APPLICATIONS

This application is a continuation-in-part of U.S. patent application Ser. No. 12/889,045, filed Sep. 23, 2010.

FIELD OF THE INVENTION

This invention pertains to the recovery of an acid catalyst from an aqueous glycolic acid mixture. More particularly, this invention pertains to a process for the extractive recovery of an acid catalyst from an aqueous glycolic acid mixture in the presence of a tertiary amine or an onium carboxylate compound, a modifier, and a diluent. The acid catalyst can be recycled to a process for the preparation of glycolic acid by the acid-catalyzed reaction of formaldehyde with carbon monoxide.

BACKGROUND OF THE INVENTION

Glycolic acid can be produced by the reaction of aqueous formaldehyde and carbon monoxide in the presence of an acid catalyst. This reaction is often referred to as the "hydrocarboxylation" or "carbonylation" of formaldehyde. The formaldehyde reactant is generally prepared by well-known methods as a aqueous mixture that contains about 35 to about 70 weight percent formaldehyde.

The hydrocarboxylation reaction is catalyzed by strong acids, either heterogeneous or homogeneous in nature. When using a homogeneous catalyst, as exemplified by sulfuric acid, the production of a purified glycolic acid product requires the removal of the acid catalyst from the reactor effluent. The glycolic acid product, however, is an unusually strong carboxylic acid (pKa approximately 3.8) and is capable of strong hydrogen-bonding and polar interactions with water. These properties make the separation and recycle of the hydrocarboxylation acid catalyst from the glycolic acid product difficult. For example, conditions that are useful for the extraction of the acid catalyst frequently will result in the coextraction of excessive amounts of glycolic acid or water with the acid catalyst. Moreover, for environmental and economic reasons, it is often desirable to isolate the strong acid catalyst in a form that permits its recycle to the hydrocarboxylation reactor.

One solution to recovering strong acid catalysts from aqueous glycolic acid reaction mixtures is to convert the acid catalyst to an easily separable or insoluble salt. For example, U.S. Pat. No. 2,153,064 discloses a process in which the crude glycolic acid effluent from a sulfuric acid-catalyzed hydrocarboxylation reaction is treated with calcium carbonate to precipitate the sulfuric acid as calcium sulfate. This inorganic salt must be separated and disposed of or sold as a low value by-product. In another example, described in U.S. Pat. No. 3,859,349, a sulfuric acid catalyst is removed the glycolic acid product mixture by absorption using a basic resin. The resin is regenerated by addition of aqueous ammonia, and the absorbed sulfuric acid is converted into ammonium sulfate, which is removed from the process. The ammonium sulfate may be sold as a fertilizer or otherwise disposed of, but is not recycled to the hydrocarboxylation reactor. Although these methods are effective for separating the acid catalysts from the glycolic acid product, they do not provide for the direct recovery and recycle of the acid catalyst to the formaldehyde hydrocarboxylation reaction. These limitations point to the need for a process in which a homogeneous acid catalyst for the hydrocarboxylation of aqueous formaldehyde with carbon monoxide can be recovered and optionally recycled in an efficient and cost-effective manner.

SUMMARY OF THE INVENTION

We have found that strong acid catalysts can be efficiently separated from aqueous mixtures of glycolic acid prepared by the hydrocarboxylation of aqueous formaldehyde solutions with carbon monoxide without extracting significant quantities of glycolic acid or other by-products. The recovered acid catalyst may be back extracted directly into aqueous formaldehyde and the resulting aqueous formaldehyde extract used as a reactant in the hydrocarboxylation reaction without further concentration. One aspect of our invention, therefore, is a process for recovering an acid catalyst from aqueous glycolic acid, comprising (A) extracting an aqueous glycolic acid mixture, comprising
  (i) about 50 to about 95 weight percent glycolic acid, based on the total weight of the aqueous glycolic acid mixture, and
  (ii) about 0.2 to about 12 weight percent, based on the total weight of the aqueous glycolic acid mixture, of an acid catalyst comprising sulfuric acid, an alkyl sulfonic acid containing from 1 to 5 carbon atoms, a fluoroalkyl sulfonic acid containing from 1 to 5 carbon atoms, or a combination thereof;
  with an extraction solvent, comprising
  (i) about 5 to about 45 weight percent, based on the total weight of the extraction solvent, of at least one tertiary amine containing from 12 to 40 carbon atoms, at least one onium carboxylate compound, or a combination thereof;
  (ii) about 5 to about 45 weight percent of at least one modifier comprising an aliphatic carboxylic acid containing from 5 to 16 carbon atoms, a fluoroalkyl carboxylic acid containing 5 to 16 carbon atoms, an organophosphorus acid containing from 5 to 16 carbon atoms, or a combination thereof; and
  (iii) about 10 to about 90 weight percent of at least one diluent comprising carbon dioxide, an aliphatic hydrocarbon containing from 3 to 25 carbon atoms, an aromatic hydrocarbon containing 6 to 25 carbon atom, a halogenated hydrocarbon containing 6 to 25 carbon atoms, or a combination thereof;
  to form an aqueous raffinate phase comprising a major amount of the glycolic acid contained in the aqueous glycolic acid mixture and an organic extract phase comprising a major amount of the acid catalyst contained in the aqueous glycolic acid mixture;
(B) separating the aqueous raffinate and organic extract phases; and
(C) extracting the organic extract phase from step (B) with an aqueous formaldehyde solution to form an aqueous formaldehyde extract comprising a major amount of the acid catalyst contained in the organic extract phase from step (B) and an organic raffinate phase comprising a minor amount of the acid catalyst contained in the organic extract phase.

Typical acid catalysts that may be recovered using the process of the invention include, but are not limited to, sulfuric acid, trifluoromethanesulfonic acid, methanesulfonic acid, methanedisulfonic acid, methylsulfonylmethanesulfonic acid, methanetrisulfonic acid, bis(methylsulfonyl)methanesulfonic acid, 1,1,2,2-tetrafluoroethanesulfonic acid, or a combination thereof. We have discovered also that a wash step can be effectively used to recover the tertiary amine and/or onium carboxylate compound and modifier from the glycolic acid raffinate to control their potential loss. Accordingly, in another embodiment of the invention, our recovery process may further comprise:

extracting the aqueous raffinate phase from step (B) with a wash solvent comprising about 80 to about 100 weight percent, based on the total weight of the wash solvent, of a wash diluent comprising carbon dioxide, an aliphatic hydrocarbon containing from 3 to 25 carbon atoms, an aromatic hydrocarbon containing 6 to 25 carbon atoms, a halogenated hydrocarbon containing 6 to 25 carbon atoms, or a combination thereof; and about 0 to about 20 weight percent of a wash modifier comprising an aliphatic carboxylic acid containing from 5 to 16 carbon atoms, an organophosphorus acid containing from 5 to 16 carbon atoms, an alkanol containing 6 to 12 carbon atoms, or a combination thereof, to form a washed aqueous raffinate phase and an organic wash extract phase, wherein the weight ratio of the wash solvent to the aqueous raffinate phase is about 0.1:1 to about 1:1;

separating the washed aqueous raffinate and organic wash extract phases, and combining the organic wash extract phase with the extraction solvent of step (A) or with the organic extract phase of step (B).

The acid catalysts that are extracted into the organic extract phase can be back extracted into aqueous formaldehyde and recycled into the hydrocarboxylation reaction. Hence, another embodiment of our invention is a process for recovering an acid catalyst from aqueous glycolic acid, comprising
(A) extracting an aqueous glycolic acid mixture, comprising
   (i) about 70 to about 90 weight percent glycolic acid, based on the total weight of the aqueous glycolic acid mixture, and
   (ii) about 1 to about 10 weight percent of an acid catalyst comprising sulfuric acid, methanesulfonic acid, methanedisulfonic acid, methanetrisulfonic acid, bis(methylsulfonyl)methanesulfonic acid, trifluoromethanesulfonic acid, 1,1,2,2-tetrafluoroethanesulfonic acid or a combination thereof;
with an extraction solvent, comprising
   (i) about 5 to about 45 weight percent, based on the total weight of the extraction solvent, a tertiary amine comprising tris(2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof;
   (ii) about 5 to about 45 weight percent of a modifier comprising 2-ethylhexanoic acid, lauric acid, perfluorooctanoic acid, bis(2-ethylhexyl)hydrogen phosphate, or a combination thereof, wherein the weight ratio of the modifier to the tertiary amine is about 1:1 to about 5:1;
   (iii) about 10 to about 90 weight percent of a diluent comprising hexane, heptane, decane, methylcyclohexane, benzene, toluene, xylene, or a combination thereof;
      to form an aqueous raffinate phase comprising a major amount of the glycolic acid contained in the aqueous glycolic acid mixture and an organic extract phase comprising a major amount of the acid catalyst contained in the aqueous glycolic acid mixture;
(B) separating the aqueous raffinate and organic extract phases;
(C) extracting the organic extract phase from step (B) with an aqueous formaldehyde solution, comprising about 35 to about 85 weight percent formaldehyde, based on the total weight of the aqueous formaldehyde solution, to form an aqueous formaldehyde extract comprising a major amount of the acid catalyst contained in the organic extract phase from step (B) and an organic raffinate phase comprising a minor amount of the acid catalyst contained in the organic extract phase;
(D) contacting the aqueous raffinate phase from step (B) with a wash solvent comprising about 80 to about 100 weight percent, based on the total weight of the wash solvent, of a wash diluent comprising hexane, heptane, decane, methylcyclohexane, benzene, toluene, xylene, or a combination thereof; and about 0 to about 20 weight percent of a wash modifier comprising 2-ethylhexanoic acid, lauric acid, bis(2-ethylhexyl)hydrogen phosphate, 2-ethylhexanol, 2-ethylbutanol, n-hexanol, n-octanol, n-decanol, or a combination thereof, to form a washed aqueous raffinate phase and an organic wash extract phase, wherein the weight ratio of the wash solvent to the aqueous raffinate phase is about 0.1:1 to about 1:1;
(E) separating the washed aqueous raffinate and organic wash extract phases; and
(F) combining the organic wash extract phase with the extraction solvent of step (A) or with the organic extract phase of step (B).

DETAILED DESCRIPTION

The present invention provides a means to recover and, optionally, recycle homogeneous, strong acid catalysts from aqueous glycolic acid mixtures that are prepared by the hydrocarboxylation of aqueous formaldehyde solutions. In a general embodiment, therefore, our invention provides a process for recovering an acid catalyst from aqueous glycolic acid, comprising:
(A) extracting an aqueous glycolic acid mixture, comprising
   (i) about 50 to about 95 weight percent glycolic acid, based on the total weight of the aqueous glycolic acid mixture, and
   (ii) about 0.2 to about 12 weight percent, based on the total weight of the aqueous glycolic acid mixture, of an acid catalyst comprising sulfuric acid, an alkyl sulfonic acid containing from 1 to 5 carbon atoms, a fluoroalkyl sulfonic acid containing from 1 to 5 carbon atoms, or a combination thereof;
with an extraction solvent, comprising
   (i) about 5 to about 45 weight percent, based on the total weight of the extraction solvent, of at least one tertiary amine containing from 12 to 40 carbon atoms, at least one onium carboxylate compound, or a combination thereof;
   (ii) about 5 to about 45 weight percent of at least one modifier comprising an aliphatic carboxylic acid containing from 5 to 16 carbon atoms, a fluoroalkyl carboxylic acid containing 5 to 16 carbon atoms, an organophosphorus acid containing from 5 to 16 carbon atoms, or a combination thereof; and
   (iii) about 10 to about 90 weight percent of at least one diluent comprising carbon dioxide, an aliphatic hydrocarbon containing from 3 to 25 carbon atoms, an aromatic hydrocarbon containing 6 to 25 carbon atom, a halogenated hydrocarbon containing 6 to 25 carbon atoms, or a combination thereof;
      to form an aqueous raffinate phase comprising a major amount of the glycolic acid contained in the aqueous glycolic acid mixture and an organic extract phase comprising a major amount of the acid catalyst contained in the aqueous glycolic acid mixture;
(B) separating the aqueous raffinate and organic extract phases; and (C) extracting the organic extract phase from step (B) with an aqueous formaldehyde solution to form an aqueous formaldehyde extract comprising a major amount of the acid catalyst contained in the organic extract phase from step (B) and an organic raffinate phase comprising a minor amount of the acid catalyst contained in the organic extract phase.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

As used in the specification and the claims, the term "feed" is intended to have its commonly understood meaning in the liquid-liquid extraction art, that is the solution that contains the materials to be extracted or separated. In the present invention, one example of a "feed" is mixture of glycolic acid, water, and sulfuric acid. The term "extraction solvent," as used herein, is intended to be synonymous with the term "extractant" and is intended to mean the immiscible liquid that is used in the extraction process to extract materials or solutes from the feed. In the present invention, one example of an extraction solvent is a solution of a tertiary amine such as tris(2-ethyl)hexylamine, a carboxylic acid modifier, such as 2-ethylhexanoic acid, and a hydrocarbon dilute, such as heptane. The term "extract" is intended to mean the immiscible liquid left from the extraction solvent after it has been contacted with the feed. The term "raffinate" is intended to mean the liquid phase left from the feed after it been contacted with the extraction solvent. The term "wash solvent" is understood to mean a liquid used to wash or enhance the purity of the raffinate phase. In the present invention, the wash solvent may contain one or more components such as, for example, tertiary amines, carboxylic acids, and hydrocarbon diluents.

The aqueous glycolic acid mixture may be prepared by any means known to persons skilled in the art such as, for example, by simply dissolving glycolic acid in water or by fermentation methods. Our invention is illustrated, however, with particular reference to recovering acid catalysts from aqueous glycolic acid mixtures prepared by contacting aqueous solutions of formaldehyde with carbon monoxide in the presence of an acid catalyst under elevated pressures and temperatures. These reactions are referred to herein as the "hydrocarboxylation" of formaldehyde and are exemplified in U.S. Pat. Nos. 2,152,852; 2,153,064; 2,211,624; 2,211,625; and 3,948,977; and United Kingdom Patent No. 1,499,245.

The hydrocarboxylation process can be carried out by feeding carbon monoxide to a reaction mixture comprising aqueous formaldehyde in the presence of an acid catalyst. The carbon monoxide typically is supplied to the reaction mixture in sufficient excess to insure an adequate supply thereof for absorption by the formaldehyde and to retard side reactions such as, for example, the decomposition of the formaldehyde to carbon monoxide and hydrogen or other products. The amount of carbon monoxide useful for the carbonylation reaction ranges from a molar ratio of about 0.1:1 to about 1,000:1 of carbon monoxide to aldehyde, formaldehyde, or formaldehyde equivalents with a more preferred range being from about 0.5:1 to about 100:1 and a most preferred range from about 1.0:1 to about 20:1.

The composition of the carbon monoxide stream required for hydrocarboxylation may comprise carbon monoxide, hydrogen, and carbon dioxide. For example, the carbon monoxide may be supplied in substantially pure form or as a mixture with other gases such as, for example, hydrogen, carbon dioxide, methane, nitrogen, noble gases (e.g., helium and argon), and the like. For example, the carbon monoxide need not be of high purity and may contain from about 1% by volume to about 99% by volume carbon monoxide. The remainder of the gas mixture may include such gases as, for example, nitrogen, hydrogen, water, noble gases, and paraffinic hydrocarbons having from one to four carbon atoms. In order to reduce compression costs, it is desirable for the carbon monoxide stream to comprise at least 95 mole % carbon monoxide, more preferably at least 99 mole %.

The carbon monoxide may be obtained from typical sources that are well known in the art. For example, the carbon monoxide may be provided by any of a number of methods known in the art including steam or carbon dioxide reforming of carbonaceous materials such as natural gas or petroleum derivatives; partial oxidation or gasification of carbonaceous materials, such as petroleum residuum, bituminous, sub bituminous and anthracitic coals and cokes, lignite, oil shale, oil sands, peat, biomass, petroleum refining residues or cokes, and the like. For example, the carbon monoxide may be provided to the reaction mixture as a component of synthesis gas or "syngas", comprising carbon dioxide, carbon monoxide, and hydrogen.

The aqueous formaldehyde used in the hydrocarboxylation reaction typically comprises about 35 to about 85 weight percent formaldehyde. Other examples of formaldehyde levels in the aqueous formaldehyde feed are about 40 to about 70 weight percent and about 40 to about 60 weight percent. These ranges are typical concentrations that can be achieved with conventional formaldehyde processes without further distillation. Conventional formaldehyde processes are described in "Formaldehyde", Kirk-Othmer Encyclopedia, Vol. 11, $4^{th}$ Edition, 1994. For example, commercially available formaldehyde typically contains approximately 55 weight percent formaldehyde in water. Other forms of formaldehyde may be present in the aqueous formaldehyde feedstock including trioxane or paraformaldehyde and linear polymers of formaldehyde, i.e., poly(oxymethylene) glycols and derivatives thereof, formed from the polymerization or oligomerization of formaldehyde in water or other solvents. The term "formaldehyde", as used herein in the context of the current specification and claims, is intended to include all the various forms of formaldehyde described above.

Examples of acid catalysts that can be used to catalyze the hydrocarboxylation reaction include, but are not limited to, sulfuric acid, trifluoromethanesulfonic acid (triflic acid), methanedisulfonic acid, methanetrisulfonic acid, methylsulfonylmethanesulfonic acid, bis(methylsulfonyl)methanesulfonic acid, 1,1,2,2-tetrafluoroethane sulfonic acid, and combinations thereof. The acids used to catalyze the hydrocarboxylation reaction and subsequently recovered by the process of the invention may be characterized as "strong" acids; that is, acids having a pKa value in water of 1 or less. For multiprotic acids, the above definition refers to the $1^{st}$ pKa value. The concentration of the strong acid catalyst species in the polar reaction product fluid may vary substantially depending on the specific strong acid catalyst species used, but typically the composition ranges from about 0.5 weight percent to about 12 weight percent. In one embodiment, for example, the acid catalyst comprises sulfuric acid at a concentration range in the hydrocarboxylation reaction mixture of about 1 to about 10 weight percent or, in another example, about 1 to about 8 weight percent, based on the total weight of the reaction mixture. In the another example, the acid catalyst comprises triflic acid having concentration of about 0.2 to about 5 weight percent or, in another example, about 0.5 to about 4 weight percent, based on the total weight of the hydrocarboxylation reaction mixture. In yet another example, the acid catalyst can comprise methanetrisulfonic acid in a concentration of about 0.5 and 10 weight percent or, in another example, about 1.0 and 8 weight percent.

The hydrocarboxylation process can be conducted under continuous, semicontinuous, and batch modes of operation and may utilize a variety of reactor types. Examples of suitable reactor types include, but are not limited to, stirred tank, continuous stirred tank, trickle bed, tower, slurry, and tubular reactors. A typical temperature range for the hydrocarboxylation reaction is about 160 to about 220° C. In another example, the temperature range can be about 190 to about 210° C. Examples of pressure ranges for the hydrocarboxylation reaction about 35 to about 350 bar gauge and about 60 to about 200 bar gauge.

The reactants and acid catalyst(s) may be introduced separately or in any sequence or combination to the reactor. In addition, one or more reactants may be introduced at different locations in the reaction zone. For example, in a continuously operated process containing a catalyst bed, the addition of water or formaldehyde may be staged throughout the reaction zone. In some cases, it may be desirable to recirculate a portion of the reaction media to the reactor to act as a liquid reaction media for the next synthesis. In order to reduce by-product formation, it is desirable to set the residence time in the hydrocarboxylation reaction to give an outlet formaldehyde concentration of about 5 weight percent or less. In addition to glycolic acid, the hydrocarboxylation process typically produces glycolic acid oligomers, water, unreacted formaldehyde, unwanted polar by-products; color bodies and corrosion metals also may be present. The polar by-products may include, but are not limited to, diglycolic acid, methoxyacetic acid, methyl methoxyacetate, and formic acid. The corrosion metals will depend on the metallurgy used for the reactor and piping and can include iron, chromium, nickel, zirconium, and combinations thereof.

For the present invention, the aqueous glycolic acid mixture comprises about 50 to about 95 weight percent glycolic acid, based on the total weight the reaction mixture. Additional examples of the concentration of glycolic acid in the aqueous mixture are about 60 to about 90 weight percent and about 65 to about 90 weight percent. For example, in one embodiment, the aqueous glycolic acid mixture comprises about 70 to about 90 weight percent glycolic acid and is produced by contacting aqueous formaldehyde with carbon monoxide in the presence of an acid catalyst as described hereinabove.

The aqueous glycolic acid mixture also comprises about 0.2 to about 12 weight percent, based on the total weight of the aqueous glycolic acid mixture, of an catalyst comprising sulfuric acid, an alkyl sulfonic acid containing from 1 to 5 carbon atoms, a fluoroalkyl sulfonic acid containing from 1 to 5 carbon atoms, or a combination thereof. Some additional examples of concentrations of the acid catalyst in the aqueous glycolic acid mixture are about 0.5 to about 10 weight percent and about 1 to about 10 weight percent. For example, the acid catalyst can comprise sulfuric acid, trifluoromethanesulfonic acid, methanesulfonic acid, methanedisulfonic acid, methanetrisulfonic acid, methylsulfonylmethanesulfonic acid, bis (methylsulfonyl)methanesulfonic acid, 1,1,2,2-tetrafluoroethanesulfonic acid, or a combination thereof. The aqueous glycolic acid solution can comprise any one of the above acids or mixtures thereof in any combination.

The aqueous glycolic acid is contacted with an extraction solvent comprising at least one tertiary amine, at least one onium carboxylate compound, or a combination thereof, and at least one diluent and at least one modifier. For example, the extraction solvent can comprise about 5 to about 45 weight percent of at least one tertiary amine containing from 12 to 40 carbon atoms, at least one onium carboxylate compound, or a combination thereof. In one embodiment, for example, the extraction solvent can comprise about 10 to about 25 weight percent of at least one tertiary amine. Some other examples of tertiary amine and/or onium carboxylate concentrations in the extraction solvent are about 5 to about 40 weight percent and about 10 to 35 weight percent. The term "tertiary amine," as used herein, is understood to mean an amine in which three carbon atoms are attached to the amino nitrogen. Typically, the tertiary amines of the invention will comprise carbon chain units that have a sufficient number of carbon atoms to facilitate their solubility in the non-polar extract phase. The carbon chain units may be linear, branched, cyclic, or a combination thereof. For example, the carbon chain units for the tertiary amines can comprise linear or branch structures, and can have in total from 12 to 40 carbon atoms. In one example, the tertiary amine can be hindered, that is, at least one of the carbon chains contains at least one branching point at the carbon at the β position from the nitrogen atom. Some representative tertiary amines include, but are not limited to, tris (2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof. In one embodiment, for example, the extraction solvent can comprise tris(2-ethylhexyl)amine.

The extraction solvent also can comprise about 5 to about 45 weight percent of at least one onium carboxylate compound that comprises a cation selected from quaternary atoms or radicals such as tertiary or quaternary ammonium, quaternary phosphonium, and trialkyl sulfonium. As noted above, additional examples of the concentration of the onium carboxylate compound in the extraction solvent are about 5 to about 40 weight percent, about 10 to about 35 weight percent, and about 10 to about 25 weight percent. The extractant may contain the onium carboxylate compound by itself or in combination with a tertiary amine as described above. The onium carboxylate compound may include the protonated forms of the above atoms or radicals and, especially, the protonated forms of various tertiary amines. Persons of skill in the art will understand that mixtures of tertiary amines and carboxylic acids will produce some quantity of onium carboxylate compounds that result from protonation of the tertiary amines by the carboxylic acid modifier and that exist in chemical equilibrium with the free amines and carboxylic acids. Therefore, in the context of the presence invention, it will be understood also by persons skilled in the art that the presence of an onium carboxylate compound in the extraction solvent that results from the protonation of a tertiary amine and a carboxylic acid is equivalent to the addition of the tertiary amine and carboxylic acid modifier separately to the extraction process. Thus, the tertiary amine and modifier can be added to the extraction process separately, as the corresponding onium carboxylate compound, or as a combination of the tertiary amine, modifier, and onium carboxylate compound.

The onium carboxylate compound may contain any number of carbon atoms, e.g., up to 60 carbon atoms, and also may contain one or more heteroatoms. The tri- and tetraalkyl quaternary ammonium and phosphonium salts typically contain a total of 5 to 40 carbon atoms. In one embodiment, for example, the onium carboxylate compound can comprise an onium cation selected from the group consisting of $R^1R^2R^3R^4N^+$, $R^1R^2R^3R^4P^+$, $R^1R^2R^3R^4As^+$, and $R^1R^2R^3S^+$, and a carboxylate anion of the type $R^5CO_2^-$, wherein $R^1$, $R^2$, $R^3$, $R^4$, and $R^5$ are independently selected from alkyl or substituted alkyl moieties having up to 20 carbon atoms, cycloalkyl or substituted cycloalkyl having 5 to 20 carbon atoms, or aryl or substituted aryl having 6 to 20 carbon atoms.

Some representative examples of ammonium cations include, but are not limited to, tetrapentylammonium, tetrahexylammonium, tetraoctylammonium, tetradecylammonium, tetradodecylammonium, tetrapropylammonium, tetrabutylammonium, methyltrioctylammonium, methyltributylammonium, N-octylquinuclidinium, N,N'-dimethyl-N,N'-dihexadecylpiperazinium diiodide, dimethylhexadecyl-[3-pyrrolidinylpropyl]ammonium, N,N,N,N',N',N'-hexa(dodecyl)octane-1,8-diammonium, and N,N,N,N',N',N'-hexa(dodecyl)butane-1,4-diammonium.

Exemplary phosphonium cations include tetraoctylphosphonium, tetrabutylphosphonium, triphenyl(hexyl)phosphonium, triphenyl(octyl)phosphonium, tribenzyl(octyl)phosphonium, tribenzyl(dodecyl)phosphonium, triphenyl(decyl)phosphonium, triphenyl(dodecyl)phosphonium, tetrakis(2-methylpropyl)phosphonium, tris(2-methylpropyl)(butyl)phosphonium, triphenyl(3,3-dimethylbutyl)phosphonium, triphenyl(3-methylbutyl)phosphonium, tris(2-methylbutyl)(3-methylbutyl)phosphonium, triphenyl[2-trimethylsilylethyl]phosphonium, tris(p-chlorophenyl)(dodecyl)phosphonium, hexyltris(2,4,6-trimethylphenyl)phosphonium, tetradecyltris(2,4,6-trimethylphenyl)phosphonium, dodecyltris(2,4,6-trimethylphenyl)phosphonium, methyltriocytlphosphonium, tetraalkylphosphonium, methyltributylphosphonium, methyltricyclohexylphosphonium, and the like. Preferred phosphonium cations include methyltriphenylphosphonium, methyltributylphosphonium, methyltriocytlphosphonium, and butyltridodecylphosphonium.

Some representative carboxylate groups include, but are not limited to, 2-ethylhexylhexanoate, n-pentanoate, 2-methylbutanoate, 3-methylbutanoate, hexanoate, 2-ethylbutanoate, heptanoate, octanoate, pelargonoate, nonanoate, decanoate, laurate, palmitate, perfluorooctanoate, or a combination thereof. In addition to the onium carboxylate compounds described above, the onium carboxylate compound may also include ammonium carboxylates salts formed from one or more of the tertiary amines and one or more aliphatic carboxylic acids described herein. For example, the onium carboxylate salt can comprise tris(2-ethylhexyl)ammonium 2-ethylhexanoate, formed from the reaction of tris(2-ethylhexyl)amine and 2-ethylhexanoic acid. In another embodiment of the invention, the acid catalyst can be triflic acid and the extraction solvent can comprise an onium carboxylate compound that comprises hydrogen tris(2-ethylhexyl)ammonium perfluorooctanoate. This latter onium carboxylate compound can be formed outside of the extraction process and added directly to the extraction solvent or formed in situ by adding tris(2-ethylhexyl)amine and perfluorooctanoic acid to the extraction solvent mixture.

In addition to at least one tertiary amine and/or onium carboxylate compound, the extraction solvent can comprise about 5 to about 45 weight percent of at least one modifier, comprising an aliphatic carboxylic acid containing from 5 to 16 carbon atoms, a fluoroalkyl carboxylic acid containing 5 to 16 carbon atoms, an organophosphorus acid containing from 5 to 16 carbon atoms, or a combination thereof. In one embodiment, the modifier does not react readily under either hydrocarboxylation or hydrogenation reaction conditions.

Some specific examples of modifiers include n-pentanoic acid, 2-methylbutanoic acid, 3-methylbutanoic acid, hexanoic acid, 2-ethylbutanoic acid, heptanoic acid, octanoic acid, 2-ethylhexanoic acid, pelargonic acid, nonanoic acid, decanoic acid, lauric acid, palmitic acid, bis(2-ethylhexyl) hydrogen phosphate, perfluorooctanoic acid, or a combination thereof. For example, in one embodiment of our process, the acid catalyst comprises trifluoromethanesulfonic acid; the tertiary amine comprises tris(2-ethylhexyl)amine; and the modifier comprises perfluorooctanoic acid. Typically, the weight ratio of the modifier to the tertiary amine, onium carboxylate compound, or the combination of the tertiary amine and the onium carboxylate compound will be in the range of about 0.1:1 to about 5:1. Some other examples of weight ratio of modifier to tertiary amine, onium carboxylate compound, or the combination thereof are about 0.5:1 to about 5:1, about 1:1 to about 5:1, and about 2:1 to about 5:1. In embodiments where the extractant comprises an onium carboxylate compound that results from the protonation of a tertiary amine with the carboxylic acid modifier, the ratio of modifier to tertiary amine may be determined from the total equivalents of tertiary amine and carboxylic acid. For example, the ratio may be determined from the weight ratio of the free tertiary amine and carboxylic acid present in extraction solvent and the weight equivalents of tertiary amine and carboxylic acid present as in form of the onium carboxylate compound.

The extraction solvent further comprises about 10 to about 90 weight percent, based on the total weight of the extraction solvent, of at least one diluent to help form an immiscible liquid phase with the aqueous glycolic acid mixture and to impart physical and transport properties that facilitate the separation of the strong acid catalyst from the glycolic acid. For example, the diluent concentration in the extraction solvent can be about 20 to about 80 weight percent. Typically, the extraction solvent can have a difference in specific gravity of at least 0.05 grams/mL with respect to the aqueous glycolic acid mixture. For example, the density of an aqueous glycolic acid mixtures, comprising typically about 70 to about 90 weight percent aqueous glycolic acid and about 1 to about 10 weight percent acid catalyst is typically in the range of about 1.1 to about 1.45 grams/mL at 40° C. In this example, the density of the extraction solvent can differ by at least 0.05 grams/mL from this range, that is density of the diluent can be less than about 1.05 g/mL or greater than about 1.50 g/mL. In another embodiment, the density of the diluent is lower than the density of the aqueous glycolic acid solution by at least 0.10 g/mL. In yet another embodiment, the density difference between the aqueous glycolic acid mixture and the diluent can be less than 0.05 grams/mL, but this may require the use of a centrifugal extractor, which can increase the cost of the process.

The diluent typically will have a low viscosity of about 10 centipoise at the extraction temperature. Some general classes of compounds that can be used as diluents in the process of the invention include carbon dioxide, aliphatic hydrocarbon containing from 3 to 25 carbon atoms, aromatic hydrocarbon containing 6 to 25 carbon atom, halogenated hydrocarbon containing 6 to 25 carbon atoms, or a combination thereof. For example, the diluent can be an aliphatic or aromatic hydrocarbon containing about 6 to about 16 carbon atoms. Mixtures of hydrocarbons may be used. Some specific, additional examples of diluents include pentane, hexane, heptane, decane, methylcyclohexane, methylene chloride, chlorobenzene, dichlorobenzene, 1,2-dichloroethane, benzene, toluene, xylene, or a combination thereof. For example, the diluent may comprise isoparaffinic mixed hydrocarbons having boiling ranges between about 90 and about 325° C., as exemplified by the ISOPAR™ solvents, such as ISOPAR™ C (boiling point range of 98 to 104° C.), ISOPAR™ E (boiling point range of 118 to 137° C.), ISOPAR™ G (boiling point range of 160 to 176° C.), ISOPAR™ H (boiling point range of 178 to 188° C.), ISOPAR™ K (boiling point range of 178 to 197° C.), ISOPAR™ L (boiling point range of 189 to 207° C.), ISOPAR™ M (boiling point range of 223 to 254° C.), and ISOPAR V (boiling point range of 273 to 312° C.).

Dense gases and supercritical fluids, for example, carbon dioxide and propane, also may be used as the diluent, either alone or in combination with other diluents. In one example of the instant invention, the acid catalyst comprises sulfuric acid; the tertiary amine comprises tris(2-ethylhexyl)amine; the modifier comprises 2-ethylhexanoic acid, and the diluent comprises hexane, heptane, decane, or a combination thereof.

The extraction of the aqueous glycolic acid mixture can be carried out by any means known in the art to intimately contact two immiscible liquid phases and to separate the resulting phases after the extraction procedure. For example, the extraction can be carried out using columns, centrifuges, mixer-settlers, and miscellaneous devices. Some representative examples of extractors include unagitated columns (e.g., spray, baffle tray and packed, perforated plate), agitated columns (e.g., pulsed, rotary agitated, and reciprocating plate), mixer-settlers (e.g., pump-settler, static mixer-settler, and agitated mixer-settler), centrifugal, and other miscellaneous extractors (e.g., emulsion phase contactor, electrically enhanced extractors, and membrane extractors). A description of these devices can be found in the *Handbook of Solvent Extraction*, Krieger Publishing Company, Malabar, F L, 1991, pp. 275-501. The various types of extractors may be used alone or in any combination.

The extraction may be conducted in one or more stages. The number of extraction stages can be selected by the best compromise between capital costs, achieving high extraction efficiency, ease of operability, and the stability of the starting materials and reaction product to the extraction conditions. The extraction also can be conducted in a batch or continuous fashion. In a continuous mode, the extraction may be carried out in a co-current, a counter-current manner, or as a fractional extraction in which multiple solvents and/or more than one solvent feed point is used to help facilitate the separation.

The aqueous glycolic acid mixture and extraction solvent can be contacted by fractional extraction methods. In this embodiment, an optional, additional polar solvent that is miscible with the aqueous glycolic acid mixture can be added to the extractor if necessary to reduce the amount of glycolic acid exiting with the organic extract phase. Some examples of polar solvents include, but are not limited to, water, ethylene glycol, glycolic acid, other liquids present in the aqueous glycolic mixture, or a combination thereof.

The extraction typically can be carried out at a temperature of about 20 to about 120° C. For example, the extraction can be conducted at a temperature of about 40 to about 85° C. The desired temperature range may be constrained further by the boiling point of the diluent component of the solvent mixture. Generally, it is undesirable to operate the extraction under conditions in which the diluent boils. The extractor for the instant invention may be operated in such a way as to establish a temperature gradient across the extractor in order to improve the mass transfer kinetics or decantation rates.

The extraction of the aqueous glycolic acid mixture produces an aqueous raffinate phase comprising a major amount of the glycolic acid contained in the aqueous glycolic acid mixture and an organic extract phase comprising a major amount of the acid catalyst contained in the aqueous glycolic acid mixture. The aqueous raffinate phase and the organic extract phase may be separated by any phase separation technology known in the art. The phase separation techniques can be accomplished in the extractor or in a separate liquid-liquid separation device. Suitable liquid-liquid separation devices include, but are not limited to, coalescers, cyclones and centrifuges. Typical equipment that can be used for liquid-liquid phase separation devices are described in the Handbook of Separation process Technology, ISBN 0-471-89558-X, John Wiley & Sons, Inc., 1987.

The acid catalyst can be back-extracted from the organic extract phase into an aqueous formaldehyde solution that subsequently can be used directly as a reactant in the hydrocarboxylation reaction. Thus, our process also comprises extracting the organic extract phase from step (B) with an aqueous formaldehyde solution to form an aqueous formaldehyde extract comprising a major amount of the acid catalyst contained in the organic extract phase from step (B) and an organic raffinate phase comprising a minor amount of the acid catalyst contained in the organic extract phase. The aqueous formaldehyde extract can be passed to a process for the preparation of glycolic acid by carbonylation of formaldehyde in the presence of an acid catalyst. Typically, the acid catalyst may be recovered at about 0.5 to about 10 weight percent in the aqueous formaldehyde extract, based on the total weight of the aqueous formaldehyde extract, and recycled to the hydrocarboxylation reaction without further concentration of the acid catalyst. The formaldehyde concentration in the aqueous formaldehyde solution generally can be about 35 to about 85 weight percent, based on the total weight of the aqueous formaldehyde solution. For example, the formaldehyde concentration can be about 40 to about 55 weight percent. This latter concentration can be obtained from conventional formaldehyde processes without further distillation. Additionally, water may be added in the aqueous formaldehyde extraction solvent if desired.

The weight ratio of the aqueous formaldehyde solution to the organic extract phase from step (B) of our inventive process about 0.05:1 to about 2:1. Further examples of weight ratios of the aqueous formaldehyde solution to the organic extract phase are about 0.1:1 to 2:1 and about 0.1:1 to about 1:1. The extraction of the acid catalyst into the aqueous formaldehyde solution can be conducted at a temperature of about 20 to about 95° C. For example, in one embodiment of the invention, steps (A)(C) of the invention are carried out at a temperature of about 40 to about 85° C. The temperature range for step (C) of the process may be constrained by the temperature at which formaldehyde begins to fall out of solution. This constraint is a function of formaldehyde concentration and is well known in the art. A description of the temperature dependency of formaldehyde solubility as a function of temperature can be found in Walker, *Formaldehyde*, Walker, ACS Monograph, Washington, D.C., ACS, 1964, p. 95. Generally, the temperature for the back extraction of the acid catalyst into the aqueous formaldehyde solution can be about 2 to about 10° C. higher than the temperature at which formaldehyde begins to fall out of solution for the chosen concentration of the aqueous formaldehyde solution. The back extraction for the instant invention may be operated in such a way as to establish a temperature gradient across the extraction vessel.

The efficacy of back extraction may be enhanced by modification of the composition of the organic extract phase from step (A) of the instant process by adding an optional non-polar additive that comprises one or more non-polar compounds or mixture of compounds. The non-polar additive can comprise the same compound or mixture of compounds used as the diluent or modifier in step (A) of the process. For example, the non-polar additive can comprise a composition which is readily recoverable by distillation of the organic raffinate phase from the back extraction step. The resulting organic raffinate phase, with or without distillation, can be recycled to the extraction in step (A) for reuse in the extraction of the aqueous glycolic acid mixture. The aqueous formaldehyde solution and the organic extract also can be contacted by fractional extraction methods. In this embodiment, a non-polar additive as described above that is miscible with the organic raffinate phase can be added to the extractor if necessary to reduce the amount of organic extract phase components (other than the acid catalyst) exiting with the aqueous formaldehyde extract.

Depending on the tertiary amine and modifier, it may be desirable to wash the aqueous raffinate in step (B) to recover any tertiary amine, onium carboxylate compound, diluent, and modifier from the aqueous raffinate phase. Our process, therefore, further comprises extracting the aqueous raffinate phase from step (B) with a wash solvent comprising about 80 to about 100 weight percent, based on the total weight of the wash solvent, of a wash diluent comprising carbon dioxide, an aliphatic hydrocarbon containing from 3 to 25 carbon atoms, an aromatic hydrocarbon containing 6 to 25 carbon atoms, a halogenated hydrocarbon containing 6 to 25 carbon atoms, or a combination thereof; and about 0 to about 20 weight percent of a wash modifier comprising an aliphatic carboxylic acid containing from 5 to 16 carbon atoms, an organophosphorus acid containing from 5 to 16 carbon atoms, an alkanol containing 6 to 12 carbon atoms, or a combination thereof, to form a washed aqueous raffinate phase and an organic wash extract phase, separating the washed aqueous raffinate and organic wash extract phases, and combining the organic wash extract phase with the extraction solvent of step (A) or with the organic extract phase of step (B).

The above wash step may be accomplished by any means known in the art such as, for example, by extracting the aqueous raffinate phase with the wash solvent in any of the various extraction centrifuges, mixer-settlers, and other extraction devices described hereinabove. The weight ratio of wash solvent to aqueous raffinate phase can be about 0.1:1 to about 1:1. An additional example of this weight ratio is about 0.2:1 to about 0.5:1. The wash step can be conducted at a temperature of about 20 to 120° C. or, in another example, at about 40 to about 85° C. As noted for the other extraction steps in present invention, the temperature range of the wash step may be limited by the boiling point of the wash solvent. Also, the wash step can be operated in such a way as to establish a temperature gradient across the wash vessel.

The wash solvent typically will comprise some or all of the same components as set forth for the extraction solvent in step (A). For example, the wash solvent can comprise about 80 to about 100 weight percent of a wash diluent that comprises carbon dioxide, an aliphatic hydrocarbons containing from 3 to 25 carbon atoms, an aromatic hydrocarbon containing 6 to 25 carbon atoms, a halogenated hydrocarbon containing 6 to 25 carbon atoms, or a combination thereof. Some representative examples of wash solvents include propane, butane, hexane, heptane, decane, methylcyclohexane, methylene chloride, chlorobenzene, dichlorobenzene, 1,2-dichloroethane, benzene, toluene, xylene, or a combination thereof. For example, the wash solvent may comprise isoparaffinic mixed hydrocarbons having boiling ranges between about 90 and about 325° C. as described previously.

The wash solvent also can comprise 0 to about 20 weight percent, based on the total weight of the wash solvent of a wash modifier. The wash modifier, typically, is a polar compound added to the wash solvent that can improve wash efficiency, i.e., the extraction of the tertiary amine, modifier, and diluent into the wash solvent. Suitable wash modifiers include carboxylic acids having from 5 to 16 carbon atoms, organophosphorus acids, alkanols having from 5 to 12 carbon atoms, or a combination thereof. Some specific examples of preferred wash modifiers include, but are not limited to n-pentanoic acid, 2-methylbutanoic acid, 3-methylbutanoic acid, hexanoic acid, perfluorooctanoic acid, 2-ethylbutanoic acid, heptanoic acid, octanoic acid, 2-ethylhexanoic acid, pelargonic acid, nonanoic acid, decanoic acid, lauric acid, palmitic acid, bis(2-ethylhexyl)hydrogen phosphate, n-hexanol, 2-ethylhexanol, 2-ethylbutanol, n-octanol, isooctanol, n-decanol, isodecanol, or a combination thereof. In one embodiment, for example, the wash solvent can comprise a composition which is readily recoverable by distillation of the organic wash extract phase from the wash step.

The wash step of this invention may be conducted in one or more extraction stages. The exact number of extraction stages will be governed by the best compromise between the capital costs of having more stages and the operating costs associated with using larger amounts of the wash solvent in order to achieve the desired extraction efficiency. The wash step may be conducted in either batch or continuous mode. When conducted continuously, the wash step may be conducted in a co-current or counter-current manner. The non-polar wash phase exiting the wash step can be fed to the primary extractor. The wash step may be performed in one or more extractors that are physically separated from the extraction of step (A) or, in another embodiment, the extraction of step (A) and the wash step can occur in the same countercurrent extractor. The wash step can be conducted in one or more of the various extractors described hereinabove for steps (A)-(C) of the instant invention.

The washed aqueous raffinate phase and the organic wash extract phase are separated and the organic wash extract may be combined with the extraction solvent of step (A) or with the organic extract phase of step (B). The washed aqueous raffinate and the organic wash extract phases can be separated by any phase separation technology known in the art and described previously herein.

Another aspect of our invention is a process for recovering an acid catalyst from aqueous glycolic acid, comprising (A) extracting an aqueous glycolic acid mixture, comprising
   (i) about 70 to about 90 weight percent glycolic acid, based on the total weight of the aqueous glycolic acid mixture, and
   (ii) about 1 to about 10 weight percent, based on the total weight of the aqueous glycolic acid mixture, of an acid catalyst comprising sulfuric acid, methanesulfonic acid, methanedisulfonic acid, methanedisulfonic acid, bis(methylsulfonyl)methanesulfonic acid, trifluoromethanesulfonic acid, 1,1,2,2-tetrafluoroethanesulfonic acid, or a combination thereof;
with an extraction solvent, comprising
   (i) about 5 to about 45 weight percent, based on the total weight of the extraction solvent, a tertiary amine comprising tris(2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof;

(ii) about 5 to about 45 weight percent of a modifier comprising 2-ethylhexanoic acid, lauric acid, perfluorooctanoic acid, bis(2-ethylhexyl)hydrogen phosphate, or a combination thereof, wherein the weight ratio of the modifier to the tertiary amine is about 1:1 to about 5:1; and (iii) about 10 to about 90 weight percent of a diluent comprising hexane, heptane, decane, methylcyclohexane, benzene, toluene, xylene, or a combination thereof;

to form an aqueous raffinate phase comprising a major amount of the glycolic acid contained in the aqueous glycolic acid mixture and an organic extract phase comprising a major amount of the acid catalyst contained in the aqueous glycolic acid mixture;

(B) separating the aqueous raffinate and organic extract phases; and (C) extracting the organic extract phase from step (B) with an aqueous formaldehyde solution, comprising about 35 to about 85 weight percent formaldehyde, based on the total weight of the aqueous formaldehyde solution, to form an aqueous formaldehyde extract comprising a major amount of the acid catalyst contained in the organic extract phase from step (B) and an organic raffinate phase comprising a minor amount of the acid catalyst contained in the organic extract phase;

(D) contacting the aqueous raffinate phase from step (B) with a wash solvent comprising about 80 to about 100 weight percent, based on the total weight of the wash solvent, of a wash diluent comprising hexane, heptane, decane, methylcyclohexane, benzene, toluene, xylene, or a combination thereof; and about 0 to about 20 weight percent of a wash modifier comprising 2-ethylhexanoic acid, lauric acid, bis(2-ethylhexyl)hydrogen phosphate, 2-ethylhexanol, 2-ethylbutanol, n-hexanol, n-octanol, n-decanol, or a combination thereof, to form a washed aqueous raffinate phase and an organic wash extract phase, wherein the weight ratio of the wash solvent to the aqueous raffinate phase is about 0.1:1 to about 1:1;

(E) separating the washed aqueous raffinate and organic wash extract phases; and (F) combining the organic wash extract phase with the extraction solvent of step (A) or with the organic extract phase of step (B).

It is understood that the above process comprises the various embodiments of the aqueous glycolic acid mixture, the acid catalyst, the tertiary amine, the modifier, diluent, and washing steps as described previously. For example, the aqueous glycolic acid mixture can be prepared by a process comprising the carbonylation of formaldehyde in the presence of a sulfuric acid catalyst. In another example, the aqueous formaldehyde solution of step (C) can comprise about 40 to about 55 weight percent formaldehyde and the aqueous formaldehyde extract of step (C) is passed to the glycolic acid process. In a further example, the catalyst can comprise sulfuric acid; the tertiary amine can comprise tris(2-ethylhexyl)amine; the modifier can comprise 2-ethylhexanoic acid; the diluent can comprise hexane, heptane, decane, or a combination thereof; the wash solvent can comprise hexane, heptane, decane, or a combination thereof; the wash modifier can comprise 2-ethylhexanoic acid, n-hexanol, n-decanol, or a combination thereof; and the weight ratio of the modifier to the tertiary amine is about 2:1 to about 4:1. The aqueous formaldehyde extract can comprise about 0.5 to about 10 weight percent sulfuric acid, based on the total weight of the aqueous formaldehyde extract.

Yet another embodiment of our invention is a process for the preparation of glycolic acid, comprising (A) contacting carbon monoxide with an aqueous formaldehyde reactant in the presence of an alkyl sulfonic acid catalyst containing from 1 to 5 carbon atoms to produce an aqueous glycolic acid mixture; and (B) recovering the alkyl sulfonic acid from the aqueous glycolic acid mixture by extracting the aqueous glycolic acid mixture with an extraction solvent comprising at least one tertiary amine, at least one onium carboxylate compound, or a combination thereof; at least one modifier comprising an aliphatic carboxylic acid, an organophosphorus acid, or a combination thereof; and at least one diluent comprising carbon dioxide, an aliphatic hydrocarbon, a halogenated hydrocarbon, or a combination thereof to form an aqueous raffinate phase comprising a major amount of the glycolic acid contained in the aqueous glycolic acid mixture and an organic extract phase comprising a major amount of the acid catalyst contained in the aqueous glycolic acid mixture.

It is understood that the above process can include the various embodiments of the hydrocarboxylation process, formaldehyde and carbon monoxide reactants, aqueous glycolic acid mixture, the sulfonic acid catalysts, reactor formats and configurations, reaction conditions of time, temperature, and pressures, extraction solvents, tertiary amines, modifiers, diluents, and wash steps as described hereinabove and in any combination. For example, as described previously, the alkyl sulfonic acid catalyst can comprise methanesulfonic acid, methanedisulfonic acid, methanetrisulfonic acid, bis(methylsulfonyl)methanesulfonic acid, methylsulfonylmethanesulfonic acid, or combinations thereof. In another example, the alkyl sulfonic acid catalyst can comprise methanesulfonic acid, methanedisulfonic acid, methanetrisulfonic acid, bis(methylsulfonyl)methanesulfonic acid, or combinations thereof. In still another example, the alkyl sulfonic acid catalyst can comprise methanetrisulfonic acid.

We have found that methanetrisulfonic acid provides higher conversions and hydrocarboxylation rates than sulfuric acid on molar basis. Accordingly, a further aspect of our invention includes a process for the preparation of glycolic acid, comprising contacting carbon monoxide with a reaction mixture comprising an aqueous formaldehyde reactant and methanetrisulfonic acid to produce an aqueous glycolic acid mixture. The above process can include the various embodiments of the hydrocarboxylation process, formaldehyde and carbon monoxide reactants, aqueous glycolic acid mixture, reactor formats and configurations, reaction conditions of time, temperature, and pressures, extraction solvents, tertiary amines, modifiers, diluents, and wash steps as described hereinabove and in any combination. For example, as described above, the hydrocarboxylation process can be carried out at a pressure of about 35 to about 350 bar gauge and a temperature of about 160 to about 220° C. and at a molar ratio of carbon monoxide to formaldehyde of about 0.5:1 to about 100:1. In still another example, the aqueous glycolic acid product can comprise about 0.2 to about 12 weight percent methanetrisulfonic acid.

A described above, we have found alkyl sulfonic acids are useful catalysts for the preparation of aqueous glycolic acid mixtures and can be efficiently recovered and recycled in accordance with the procedures described hereinabove. Thus, another embodiment of our invention is a process for the preparation of glycolic acid, comprising (A) contacting carbon monoxide with an aqueous formaldehyde reactant in the presence of an acid catalyst comprising methanesulfonic acid, methanedisulfonic acid, methanetrisulfonic acid, bis(methylsulfonyl)methanesulfonic acid, or a combination thereof to produce an aqueous glycolic acid mixture comprising about 70 to about 90 weight percent glycolic acid, based on the total weight of the aqueous glycolic acid mixture, and about 1 to about 10 weight percent of the acid catalyst;

(B) extracting the aqueous glycolic acid mixture with an extraction solvent, comprising
  (i) about 5 to about 45 weight percent, based on the total weight of the extraction solvent, of a tertiary amine comprising tris(2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof;
  (ii) about 5 to about 45 weight percent, based on the total weight of the extraction solvent, of a modifier comprising 2-ethylhexanoic acid, lauric acid, bis(2-ethylhexyl) hydrogen phosphate, perfluorooctanoic acid, or a combination thereof, wherein the weight ratio of the modifier to the tertiary amine is about 1:1 to about 5:1; and
  (iii) about 10 to about 90 weight percent of a diluent, based on the total weight of the extraction solvent, comprising hexane, heptane, decane, methylcyclohexane, benzene, toluene, xylene, isoparaffinic mixed hydrocarbons having a boiling range between 90 and 325° C., or a combination thereof;
  to form an aqueous raffinate phase comprising a major amount of the glycolic acid contained in the aqueous glycolic acid mixture and an organic extract phase comprising a major amount of the acid catalyst contained in the aqueous glycolic acid mixture;

(C) separating the aqueous raffinate and organic extract phases; and (D) extracting the organic extract phase from step (C) with an aqueous formaldehyde solution, comprising about 35 to about 85 weight percent formaldehyde, based on the total weight of the aqueous formaldehyde solution, to form an aqueous formaldehyde extract comprising a major amount of the acid catalyst contained in the organic extract phase from step (C) and an organic raffinate phase comprising a minor amount of the acid catalyst contained in the organic extract phase.

It is understood that the above process can include the various embodiments of the hydrocarboxylation process, formaldehyde and carbon monoxide reactants, aqueous glycolic acid mixture, the sulfonic acid catalysts, reactor formats and configurations, reaction conditions of time, temperature, and pressures, extraction solvents, tertiary amines, modifiers, diluents, and wash steps as described hereinabove and in any combination. For example, as described previously, the acid catalyst can comprise methanetrisulfonic acid.

The invention also includes the following embodiments 1-34 set forth below. Embodiment 1 is a process for recovering an acid catalyst from aqueous glycolic acid, comprising:

(A) extracting an aqueous glycolic acid mixture, comprising
  (i) about 50 to about 95 weight percent glycolic acid, based on the total weight of the aqueous glycolic acid mixture, and
  (ii) about 0.2 to about 12 weight percent, based on the total weight of the aqueous glycolic acid mixture, of an acid catalyst comprising sulfuric acid, an alkyl sulfonic acid containing from 1 to 5 carbon atoms, a fluoroalkyl sulfonic acid containing from 1 to 5 carbon atoms, or a combination thereof;
  with an extraction solvent, comprising
  (i) about 5 to about 45 weight percent, based on the total weight of the extraction solvent, of at least one tertiary amine containing from 12 to 40 carbon atoms, at least one onium carboxylate compound, or a combination thereof;
  (ii) about 5 to about 45 weight percent of at least one modifier comprising an aliphatic carboxylic acid containing from 5 to 16 carbon atoms, a fluoroalkyl carboxylic acid containing 5 to 16 carbon atoms, an organophosphorus acid containing from 5 to 16 carbon atoms, or a combination thereof; and
  (iii) about 10 to about 90 weight percent of at least one diluent comprising carbon dioxide, an aliphatic hydrocarbon containing from 3 to 25 carbon atoms, an aromatic hydrocarbon containing 6 to 25 carbon atom, a halogenated hydrocarbon containing 6 to 25 carbon atoms, or a combination thereof;
  to form an aqueous raffinate phase comprising a major amount of the glycolic acid contained in the aqueous glycolic acid mixture and an organic extract phase comprising a major amount of the acid catalyst contained in the aqueous glycolic acid mixture;

(B) separating the aqueous raffinate and organic extract phases; and (C) extracting the organic extract phase from step (B) with an aqueous formaldehyde solution to form an aqueous formaldehyde extract comprising a major amount of the acid catalyst contained in the organic extract phase from step (B) and an organic raffinate phase comprising a minor amount of the acid catalyst contained in the organic extract phase.

Embodiment 2 is a process that includes the features of embodiment 1 in which the aqueous glycolic acid mixture comprises about 70 to about 90 weight percent glycolic acid and is produced by contacting aqueous formaldehyde with carbon monoxide in the presence of an acid catalyst.

Embodiment 3 is a process that includes the features of any one of embodiments 1 and 2, in which the acid catalyst comprises sulfuric acid, trifluoromethanesulfonic acid, methanesulfonic acid, methanedisulfonic acid, methanetrisulfonic acid, bis(methylsulfonyl)methanesulfonic acid, 1,1,2,2-tetrafluoroethanesulfonic acid, or a combination thereof.

Embodiment 4 is a process that includes the features of any one of embodiments 1-3, in which the tertiary amine comprises tris(2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof.

Embodiment 5 is a process that includes the features of any one of embodiments 1-4, in which the modifier comprises n-pentanoic acid, 2-methylbutanoic acid, 3-methylbutanoic acid, hexanoic acid, 2-ethylbutanoic acid, heptanoic acid, octanoic acid, 2-ethylhexanoic acid, pelargonic acid, nonanoic acid, decanoic acid, lauric acid, palmitic acid, bis(2-ethylhexyl)hydrogen phosphate, perfluorooctanoic acid, or a combination thereof.

Embodiment 6 is a process that includes the features of any one of embodiments 1-5, in which the diluent comprises pentane, hexane, heptane, decane, methylcyclohexane, methylene chloride, chlorobenzene, dichlorobenzene, 1,2-dichloroethane, benzene, toluene, xylene, or a combination thereof.

Embodiment 7 is a process that includes the features of any one of embodiments 1-6, in which the aqueous formaldehyde solution comprises about 35 to about 85 weight percent formaldehyde, the aqueous formaldehyde extract comprises about 0.5 to about 10 weight percent, based on the total weight of the aqueous formaldehyde extract, of the acid catalyst, and the weight ratio of the aqueous formaldehyde solution to the organic extract phase is about 0.1:1 to about 1:1.

Embodiment 8 is a process that includes the features of any one of embodiments 1-7, in which the acid catalyst comprises trifluoromethanesulfonic acid; the tertiary amine comprises tris(2-ethylhexyl)amine; and the modifier comprises perfluorooctanoic acid.

Embodiment 9 is a process that includes the features of any one of embodiments 1-8, in which the acid catalyst comprises sulfuric acid; the tertiary amine comprises tris(2-ethylhexyl) amine; the modifier comprises 2-ethylhexanoic acid, and the diluent comprises hexane, heptane, decane, or a combination thereof.

Embodiment 10 is a process that includes the features of any one of embodiments 1-9, wherein steps (A) and (C) are carried out at a temperature of about 40 to about 85° C.

Embodiment 11 is a process that includes the features of any one of embodiments 1-10, in which the aqueous formaldehyde extract is passed to a process for the preparation of glycolic acid by the carbonylation of formaldehyde in the presence of an acid catalyst.

Embodiment 12 is a process that includes the features of any one of embodiments 1-11 that further comprises extracting the aqueous raffinate phase from step (B) with a wash solvent comprising about 80 to about 100 weight percent, based on the total weight of the wash solvent, of a wash diluent comprising carbon dioxide, an aliphatic hydrocarbon containing from 3 to 25 carbon atoms, an aromatic hydrocarbon containing 6 to 25 carbon atoms, a halogenated hydrocarbon containing 6 to 25 carbon atoms, or a combination thereof; and about 0 to about 20 weight percent of a wash modifier comprising an aliphatic carboxylic acid containing from 5 to 16 carbon atoms, an organophosphorus acid containing from 5 to 16 carbon atoms, an alkanol containing 6 to 12 carbon atoms, or a combination thereof, to form a washed aqueous raffinate phase and an organic wash extract phase, wherein the weight ratio of the wash solvent to the aqueous raffinate phase is about 0.1:1 to about 1:1;
separating the washed aqueous raffinate and organic wash extract phases, and
combining the organic wash extract phase with the extraction solvent of step (A) or with the organic extract phase of step (B).

Embodiment 13 is a process that includes the features of embodiment 12, in which the wash solvent comprises propane, butane, hexane, heptane, decane, methylcyclohexane, methylene chloride, chlorobenzene, dichlorobenzene, 1,2-dichloroethane, benzene, toluene, xylene, or a combination thereof; and the wash modifier comprises n-pentanoic acid, 2-methylbutanoic acid, 3-methylbutanoic acid, hexanoic acid, perfluorooctanoic acid, 2-ethylbutanoic acid, heptanoic acid, octanoic acid, 2-ethylhexanoic acid, pelargonic acid, nonanoic acid, decanoic acid, lauric acid, palmitic acid, bis(2-ethylhexyl)hydrogen phosphate, n-hexanol, 2-ethylhexanol, 2-ethylbutanol, n-octanol, isooctanol, n-decanol, isodecanol, or a combination thereof.

Embodiment 14 is a process that includes the features of embodiment 1, in which the aqueous glycolic acid mixture, comprises:
(i) about 70 to about 90 weight percent glycolic acid, based on the total weight of the aqueous glycolic acid mixture, and
(ii) about 1 to about 10 weight percent of an acid catalyst comprising sulfuric acid, methanesulfonic acid, methanedisulfonic acid, methanedisulfonic acid, bis(methylsulfonyl)methanesulfonic acid, trifluoromethanesulfonic acid, 1,1,2,2-tetrafluoroethanesulfonic acid, or a combination thereof;
the extraction solvent, comprises:
(i) a tertiary amine comprising tris(2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof;
(ii) a modifier comprising 2-ethylhexanoic acid, lauric acid, perfluorooctanoic acid, bis(2-ethylhexyl)hydrogen phosphate, or a combination thereof; and
(iii) a diluent comprising hexane, heptane, decane, methylcyclohexane, benzene, toluene, xylene, or a combination thereof; in which the aqueous formaldehyde solution of step C comprises about 35 to about 85 weight percent formaldehyde, based on the total weight of the aqueous formaldehyde solution;
and wherein the process further comprises:
(D) contacting the aqueous raffinate phase from step (B) with a wash solvent comprising about 80 to about 100 weight percent, based on the total weight of the wash solvent, of a wash diluent comprising hexane, heptane, decane, methylcyclohexane, benzene, toluene, xylene, or a combination thereof; and about 0 to about 20 weight percent of a wash modifier comprising 2-ethylhexanoic acid, lauric acid, bis(2-ethylhexyl)hydrogen phosphate, 2-ethylhexanol, 2-ethylbutanol, n-hexanol, n-octanol, n-decanol, or a combination thereof, to form a washed aqueous raffinate phase and an organic wash extract phase, wherein the weight ratio of the wash solvent to the aqueous raffinate phase is about 0.1:1 to about 1:1;
(E) separating the washed aqueous raffinate and organic wash extract phases; and
(F) combining the organic wash extract phase with the extraction solvent of step (A) or with the organic extract phase of step (B).

Embodiment 15 is a process that includes the features of embodiment 14, wherein:
the aqueous glycolic acid mixture is prepared by process comprising the carbonylation of formaldehyde in the presence of a sulfuric acid catalyst;
the aqueous formaldehyde solution of step (C) comprises about 40 to about 55 weight percent formaldehyde and the aqueous formaldehyde extract of step (C) is passed to the glycolic acid process;
the acid catalyst comprises sulfuric acid; the tertiary amine comprises tris(2-ethylhexyl)amine; the modifier comprises 2-ethylhexanoic acid;
the diluent comprises hexane, heptane, decane, or a combination thereof; the wash solvent comprises hexane, heptane, decane, or a combination thereof; the wash modifier comprises 2-ethylhexanoic acid, n-hexanol, n-decanol, or a combination thereof; and the weight ratio of the modifier to the tertiary amine is about 2:1 to about 4:1; and
the aqueous formaldehyde extract comprises about 0.5 to about 10 weight percent sulfuric acid, based on the total weight of the aqueous formaldehyde extract.

Embodiment 16 is a process for the preparation of glycolic acid, comprising
(A) contacting carbon monoxide with an aqueous formaldehyde reactant in the presence of an alkyl sulfonic acid catalyst containing from 1 to 5 carbon atoms to produce an aqueous glycolic acid mixture; and
(B) recovering the alkyl sulfonic acid from the aqueous glycolic acid mixture by extracting the aqueous glycolic acid mixture with an extraction solvent comprising at least one tertiary amine, at least one onium carboxylate compound or a combination thereof; at least one modifier comprising an aliphatic carboxylic acid, an organophosphorus acid, or a combination thereof; and at least one diluent comprising carbon dioxide, an aliphatic hydrocarbon, a halogenated hydrocarbon, or a combination thereof to form an aqueous raffinate phase comprising a major amount of the glycolic acid contained in the aqueous glycolic acid mixture and an organic extract phase comprising a major amount of the acid catalyst contained in the aqueous glycolic acid mixture.

Embodiment 17 is a process that includes the features of embodiment 16, in which the molar ratio of carbon monoxide to formaldehyde is about 0.5:1 to about 100:1, and the contacting is at a pressure of about 35 to about 350 bar gauge and a temperature of about 160 to about 220° C.

Embodiment 18 is a process that includes the features of any one of embodiments 16 and 17, in which the aqueous glycolic acid mixture comprises about 50 to about 95 weight percent glycolic acid and about 0.2 to about 12 weight percent of the alkyl sulfonic acid catalyst, each based on the total weight of the aqueous glycolic acid mixture.

Embodiment 19 is a process that includes the features of any one of embodiments 16-18, in which the alkyl sulfonic acid catalyst comprises methanesulfonic acid, methanedisulfonic acid, methanetrisulfonic acid, bis(methylsulfonyl)methanesulfonic acid, methylsulfonylmethanesulfonic acid, or combinations thereof.

Embodiment 20 is a process that includes the features of any one of embodiments 16-19, in which the alkyl sulfonic acid catalyst comprises methanesulfonic acid, methanedisulfonic acid, methanetrisulfonic acid, bis(methylsulfonyl)methanesulfonic acid, or combinations thereof.

Embodiment 21 is a process that includes the features of any one of embodiments 16-20, in which the alkyl sulfonic acid catalyst comprises methanetrisulfonic acid.

Embodiment 22 is a process that includes the features of any one of embodiments 16-21, in which the tertiary amine comprises tris(2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof.

Embodiment 23 is a process that includes the features of any one of embodiments 16-22, in which the modifier comprises n-pentanoic acid, 2-methylbutanoic acid, 3-methylbutanoic acid, hexanoic acid, 2-ethylbutanoic acid, heptanoic acid, octanoic acid, 2-ethylhexanoic acid, pelargonic acid, nonanoic acid, decanoic acid, lauric acid, palmitic acid, bis(2-ethylhexyl)hydrogen phosphate, perfluorooctanoic acid, or a combination thereof.

Embodiment 24 is a process that includes the features of any one of embodiments 16-23, in which the diluent comprises pentane, hexane, heptane, decane, methylcyclohexane, methylene chloride, chlorobenzene, dichlorobenzene, 1,2-dichloroethane, benzene, toluene, xylene, isoparaffinic mixed hydrocarbons having a boiling range between 90 and 325° C., or a combination thereof.

Embodiment 25 is a process that includes the features of any one of embodiments 16-24 and further comprises
(C) separating the aqueous raffinate and organic extract phases; and
(D) extracting the organic extract phase from step (C) with an aqueous formaldehyde solution to form an aqueous formaldehyde extract comprising a major amount of the acid catalyst contained in the organic extract phase from step (C) and an organic raffinate phase comprising a minor amount of the acid catalyst contained in the organic extract phase.

Embodiment 26 is a process that includes the features of embodiment 25, in which the aqueous formaldehyde solution comprises about 35 to about 85 weight percent formaldehyde, based on the total weight of the aqueous formaldehyde solution, the aqueous formaldehyde extract comprises about 0.5 to about 10 weight percent, based on the total weight of the aqueous formaldehyde extract, of the alkyl sulfonic acid catalyst, and the weight ratio of the aqueous formaldehyde solution to the organic extract phase is about 0.1:1 to about 1:1.

Embodiment 27 is a process that includes the features of any one of embodiments 25-26, in which the aqueous formaldehyde extract is recycled to step (A).

Embodiment 28 is a process for the preparation of glycolic acid, comprising contacting carbon monoxide with a reaction mixture comprising an aqueous formaldehyde reactant and methanetrisulfonic acid to produce to produce an aqueous glycolic acid mixture.

Embodiment 29 is a process that includes the features of embodiment 28, in which the molar ratio of carbon monoxide to formaldehyde is about 0.5:1 to about 100:1, the contacting is at a pressure of about 35 to about 350 bar gauge and a temperature of about 160 to about 220° C., and the concentration of methanetrisulfonic acid in the aqueous glycolic acid mixture is about 0.2 to about 12 weight percent.

Embodiment 30 is a process for the preparation of glycolic acid, comprising (A) contacting carbon monoxide with an aqueous formaldehyde reactant in the presence of an acid catalyst comprising methanesulfonic acid, methanedisulfonic acid, methanetrisulfonic acid, bis(methylsulfonyl)methanesulfonic acid, or a combination thereof to produce an aqueous glycolic acid mixture comprising about 70 to about 90 weight percent glycolic acid, based on the total weight of the aqueous glycolic acid mixture, and about 1 to about 10 weight percent of the acid catalyst;
(B) extracting the aqueous glycolic acid mixture with an extraction solvent, comprising
  (i) about 5 to about 45 weight percent, based on the total weight of the extraction solvent, of a tertiary amine comprising tris(2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof;
  (ii) about 5 to about 45 weight percent, based on the total weight of the extraction solvent, of a modifier comprising 2-ethylhexanoic acid, lauric acid, bis(2-ethylhexyl)hydrogen phosphate, perfluorooctanoic acid, or a combination thereof, wherein the weight ratio of the modifier to the tertiary amine is about 1:1 to about 5:1; and
  (iii) about 10 to about 90 weight percent of a diluent, based on the total weight of the extraction solvent, comprising hexane, heptane, decane, methylcyclohexane, benzene, toluene, xylene, isoparaffinic mixed hydrocarbons having a boiling range between 90 and 325° C., or a combination thereof;
  to form an aqueous raffinate phase comprising a major amount of the glycolic acid contained in the aqueous glycolic acid mixture and an organic extract phase comprising a major amount of the acid catalyst contained in the aqueous glycolic acid mixture;
(C) separating the aqueous raffinate and organic extract phases; and
(D) extracting the organic extract phase from step (C) with an aqueous formaldehyde solution, comprising about 35 to about 85 weight percent formaldehyde, based on the total weight of the aqueous formaldehyde solution, to form an aqueous formaldehyde extract comprising a major amount of the acid catalyst contained in the organic extract phase from step (C) and an organic raffinate phase comprising a minor amount of the acid catalyst contained in the organic extract phase.

Embodiment 31 is a process that includes the features of embodiment 30 and further comprises
(E) contacting the aqueous raffinate phase from step (C) with a wash solvent comprising about 80 to about 100 weight percent, based on the total weight of the wash solvent, of a wash diluent comprising hexane, heptane, decane, methylcyclohexane, benzene, toluene, xylene, isoparaffinic mixed hydrocarbons having a boiling range between 90 and 325° C., or a combination thereof; and about 0 to about 20 weight percent of a wash modifier comprising 2-ethylhexanoic acid, lauric acid, bis(2-ethylhexyl)hydrogen phosphate, 2-ethylhexanol, 2-ethylbutanol, n-hexanol, n-octanol, n-decanol, or a combination thereof, to form a washed aqueous raffinate phase and an organic wash extract phase, wherein the weight ratio of the wash solvent to the aqueous raffinate phase is about 0.1:1 to about 1:1;

(F) separating the washed aqueous raffinate and organic wash extract phases; and (G) combining the organic wash extract phase with the extraction solvent of step (B) or with the organic extract phase of step (C).

Embodiment 32 is a process that includes the features of any one of embodiments 30 and 31, in which the acid catalyst comprises methanetrisulfonic acid.

Embodiment 33 is a process that includes the features of any one of embodiments 30-32, in which the tertiary amine comprises tris(2-ethylhexyl)amine; the modifier comprises 2-ethylhexanoic acid; the diluent comprises hexane, heptane, decane, or a combination thereof; the wash solvent comprises hexane, heptane, decane, isoparaffinic mixed hydrocarbons having a boiling range between 90 and 325° C., or a combination thereof; the wash modifier comprises 2-ethylhexanoic acid, n-hexanol, n-decanol, or a combination thereof; and the weight ratio of the modifier to the tertiary amine is about 2:1 to about 4:1.

Embodiment 34 is a process that includes the features of any one of embodiments 30-33, in which the aqueous formaldehyde solution of step (D) comprises about 40 to about 55 weight percent formaldehyde and the aqueous formaldehyde extract of step (D) is passed to step (A).

The principles laid out in the instant invention are further illustrated by the following examples.

EXAMPLES

General

Glycolic acid solutions and extraction samples were analyzed by liquid chromatography. Quantitation of analytes comprising glycolic acid, glycolate oligomers, and related species was performed using ion-exclusion chromatography after samples were subjected to acid hydrolysis in aqueous 25% v/v $H_2SO_4$ at 80° C. for 30 minutes. The analytes were separated on a Hamilton PRP X300 column using a 10 mM $H_3PO_4$ mobile phase with a 1-20% v/v acetonitrile gradient. The eluting components were monitored using a UV detector set at 210 nm and their concentrations calculated based on calibration using external standards. Formaldehyde was determined by liquid chromatographic separation of the 2,4-dinitrophenylhydrazone derivative of formaldehyde and its subsequent detection by UV at 360 nm. The same acid hydrolysate from the procedure above was reacted with dinitrophenylhydrazine, then analyzed using a Phenomenex Luna C8 column using a 1:1 water:acetonitrile mobile phase under isocratic conditions. The formaldehyde concentration was calculated based on calibration using external standards.

Reactor effluent and extraction samples also were analyzed for sulfur using a wavelength dispersive x-ray fluorescence (WDXRF) semi-quantitative application called UNI-QUANT™ (UQ). UQ affords standardless XRF analysis of samples. The data were mathematically corrected for matrix differences between calibration standards and samples as well as absorption and enhancement effects; i.e., inter-element effects. Instrument conditions for sulfur analysis were: Line, $K_a$; kV, 40; mA, 60; Filter, none; Collimator Spacing (mm), 150; Crystal, Ge III-C; Peak Angle (2q), 110.6712; Detector, flow; PHD Lower, 35; PHD Upper, 70; Collimator Mask (mm), 30; Peak time (s), 30.

Extractor samples were diluted in isopropyl alcohol to minimize matrix effects and analyzed quantitatively using WDXRF. The WDXRF calibrations were performed using serial dilutions of stock standards prepared wt./wt. and certified using ICP-OES. Instrument conditions for sulfur analysis were: Line, $K_a$; kV, 50; mA, 60; Filter, none; Collimator Spacing (mm), 700; Crystal, Graphite; Peak Angle (2q), 106.4608; —offset, 2.6696; Detector, flow; PHD Lower, 27; PHD Upper, 75; Collimator Mask (mm), 30; —Offset time (s), 10; Peak time (s), 50.

For all extraction examples, the molar selectivity for the tertiary amine-containing phase (i.e., extraction solvent) for sulfuric acid ($H_2SO_4$) over glycolic acid (GA) is defined as follows:

$$\text{Molar Selectivity} = \frac{(\text{Moles } H_2SO_4 \text{ in amine phase}) \times (\text{Moles } GA \text{ in aqueous } GA \text{ Phase})}{(\text{Moles } H_2SO_4 \text{ in aq. } GA \text{ phase}) \times (\text{Moles } H_2SO_4 \text{ in amine phase})}$$

Throughout the examples, the following abbreviations are used in the Tables:
HFr=formaldehyde
GA=glycolic acid and oligomers
HOFr=formic acid
DGA=diglycolic acid
MAA=methoxyacetic acid
TfOH=trifluoromethanesulfonic acid or triflic acid
PFOA-H=perfluorooctanoic acid
TEHA=tris(2-ethylhexyl)amine
2-EHA=2-ethylhexanoic acid
DEHPA=bis(2-ethylhexyl)hydrogen phosphate
MTSA=methanetrisulfonic acid
MDSA=methanedisulfonic acid
MMSA=methylsulfonylmethanesulfonic acid
BMMSA=bis(methylsulfonyl)methanesulfonic acid Examples 1-4

Preparation of Aqueous Glycolic Acid Solutions—Hydrocarboxylation reactor effluents were prepared for subsequent extraction experiments in the following manner for Examples 1-4: A mixture comprising formaldehyde, water, glycolic acid, and acid catalyst was fed continuously to a high pressure zirconium autoclave, nominally 125 mL volume, fitted with a hollow shaft Rushton turbine impeller (for gas introduction and dispersion), baffles, thermo well, gas inlet tube, and sip tube to maintain liquid level at approximately 90 mL and to provide an exit for product effluent. The autoclave was heated electrically by a band heater, with temperature control provided by feedback via a K-type thermocouple in the autoclave thermo well. Pure carbon monoxide gas (>99.9%) was fed to the autoclave via a Brooks flow controller. Reactor effluent passed through zirconium tubing, maintained at 60° C., an automatic pressure control valve, and into a Hastelloy collection vessel (1 liter), also maintained at 60° C. The collection vessel was drained every six hours and analyzed by liquid chromatography, gas chromatography, and X-ray sulfur analysis to determine product composition. If conditions of feed flow rate, reactor temperature or pressure, gas flow rate, agitation rate were changed, the reactor was assumed to be at steady state operation after 6 to 10 reactor volumes of feed had been passed through the reactor. Feed conditions and product analyses are given in Table 1 and Table 2 respectively.

TABLE 1

Reaction Conditions for the Preparation of Glycolic Acid

| Example | T, °C. | P, bara | Residence time, min | Glycolic Acid | HFr (as 100% HFr) | Water | Acid Catalyst |
|---|---|---|---|---|---|---|---|
| 1 | 180 | 135 | 92 | 2.0 | 1.0 | 1.0 | 0.10 ($H_2SO_4$) |
| 2 | 190 | 132 | 92 | 2.0 | 1.0 | 1.4 | 0.10 ($H_2SO_4$) |
| 3 | 190 | 132 | 92 | 2.0 | 1.0 | 2.2 | 0.09 ($H_2SO_4$) |
| 4 | 205 | 180 | 55 | 2.0 | 1.0 | 2.2 | 0.09 (TfOH) |

TABLE 2

Analysis of Glycolic Acid Reaction Mixtures

| Example | % HFr Conversion | HFr Selectivity to GA | GA | HFr | Sum of DGA, HOFR, MAA | Acid Catalyst |
|---|---|---|---|---|---|---|
| 1 | 92.0% | 93.6% | 88.6% | 0.9% | 1.7% | 3.3% |
| 2 | 93.1% | 87.0% | 84.6% | 0.8% | 2.0% | 4.0% |
| 3 | 90.0% | 84.5% | 80.8% | 1.3% | 1.9% | 3.9% |
| 4 | 94.2% | 89.2% | 80.3% | 0.66% | 1.5% | 3.1% |

Example 5

The reactor effluent generated in Example 1, comprising 3.3 wt % sulfuric acid in crude aqueous glycolic acid, was subjected to a series of twenty-four cross-flow batch extractions using the following procedure to simulate a six-stage continuous countercurrent extraction process with the reactor effluent feed on stage one and the extraction solvent mixture introduced on stage six. The reactor effluent generated in Reaction Example 1, comprising 3.3 wt % sulfuric acid in crude aqueous glycolic acid, was subjected to a cascaded series of twenty-four cross-flow batch extractions to simulate a six-stage continuous countercurrent extraction process, with the reactor effluent feed on stage one, and the amine solvent mixture introduced on stage six. The multi-cycle, cascaded pattern of 24 extractions in which multiple fresh feed and solvent charges are introduced at separate ends of each cycle of the cascade, and with raffinate and extract compositions introduced to the next cycle of the cascade, results in a set of conditions on the final cycle which have been shown to closely approach the equilibrium composition profile of a continuous, staged counter-current extractor. For this work, with the relatively high partition coefficient of sulfuric acid into the amine solvent mixture, three cycles were found to be sufficient to asymptotically approach continuous extraction equilibrium conditions. The simulated countercurrent extraction technique used herein is well-known to those skilled in the art and is laid out in detail in Treybal, *Liquid Extraction*, 2$^{nd}$ Ed., McGraw-Hill, New York, N.Y., 1963, pp. 349-366.

The pattern of 24 extractions results in a final set of conditions which have been shown to closely approach the equilibrium composition profile of a continuous six stage countercurrent extractor. The extraction solvent comprised a mixture of 35 wt % tris(2-ethylhexyl) amine ("TEHA"), 32.5 wt % 2-ethylhexanoic acid ("2-EHA"), and 32.5 wt % heptane. The solvent to feed weight ratio was 0.5:1. The final simulated extract and raffinate streams were subjected to liquid chromatography and X-ray sulfur analysis to determine the compositions of the products. None of the extractions exhibited the formation of three liquid phases. The recovery of the sulfuric acid from the hydrocarboxylation reactor effluent to the organic extract product was 92.3%, and 95.2% of the feed glycolic acid was recovered in the raffinate. The molar selectivity of the extraction solvent for sulfuric acid over glycolic acid was 19.3.

Example 6

The reactor effluent generated in Example 1 was subjected to a series of twenty-four cross-flow batch extractions using the same procedure of Example 5 to simulate a six-stage continuous countercurrent extraction process, with the reactor effluent feed on stage one, and the extraction solvent mixture introduced on stage six. The extraction solvent comprised a mixture of 35 wt % tris(2-ethylhexyl)amine, 32.5 wt % 2-ethylhexanoic acid, and 32.5 wt % heptane. The extraction solvent to feed weight ratio was 0.67:1.0. The final simulated extract and raffinate streams were subjected to liquid chromatography and X-ray sulfur analysis to determine the compositions of the products. None of the extractions exhibited the formation of three liquid phases. The recovery of the sulfuric acid from the hydrocarboxylation reactor effluent to the organic extract phase was 98.1%; 99.2% of the feed glycolic acid in the reactor effluent was recovered in the raffinate. The molar selectivity of the extraction solvent for sulfuric acid over glycolic acid was 119.4.

Example 7

The reactor effluent generated in Example 2, comprising 4.0 wt % sulfuric acid in crude aqueous glycolic acid, was subjected to a series of twenty-four cross-flow batch extractions at 40° C. using the procedure laid out in Example 5 to simulate a six-stage continuous countercurrent extraction process, with the reactor effluent feed on stage one, and the extraction solvent mixture introduced on stage six. The extraction solvent contained a mixture of 35 wt % tris(2-ethylhexyl)amine, 32.5 wt % bis(2-ethylhexyl)hydrogen phosphate ("DEHPA") and 32.5 wt % heptane. The extraction solvent to feed weight ratio was 0.67:1.0. The final extract and raffinate streams were subjected to liquid chromatography and X-ray sulfur analysis to determine the compositions of the products. None of the extractions exhibited the formation of three liquid phases. The recovery of the sulfuric acid from the hydrocarboxylation reactor effluent to the organic extract phase was 98.5%; 95.7% of the feed glycolic acid was recovered in the raffinate. The molar selectivity of the extraction solvent for sulfuric acid over glycolic acid was 23.2.

Example 8

Back extraction simulation with DEHPA and HFr—The reactor effluent generated in Example 2, comprising 4.0 wt % sulfuric acid in crude aqueous glycolic acid, was subjected to a single cross flow extraction with an extraction solvent containing 35 wt % tris(2-ethylhexyl)amine, 32.0 wt % bis(2-ethylhexyl)hydrogen phosphate and 33.0 wt % heptane. The extraction solvent to feed weight ratio was 0.45:1.0. This extraction recovered 64% of the sulfuric acid that was present in the aqueous glycolic acid feed into the organic extract phase. The organic extract phase from the cross flow extraction, containing 6.2 weight % $H_2SO_4$ as a tertiary amine-acid complex, was then subjected to a series of twenty-four cross-flow batch extractions at 75° C. using the procedure set forth in Example 5 to simulate a six-stage continuous countercurrent extraction process with the organic extract phase on stage one, and aqueous formaldehyde solution introduced on stage six. The formaldehyde solution was a mixture of 42 wt % formaldehyde in water, generated by the partial oxidation of methanol over a commercial mixed metal oxide formaldehyde catalyst. The formaldehyde solution extractant to feed weight ratio was 0.67:1.0. The final simulated extract and raffinate streams were subjected to liquid chromatography and X-ray sulfur analysis to determine the compositions of the products. None of the extractions exhibited the formation of three liquid phases. The recovery of the sulfuric acid from the organic extract phase to the aqueous formaldehyde extract was 98.7%. The sulfuric acid content of the organic raffinate phase was 820 ppm after extraction and the concentration of sulfuric acid in the aqueous formaldehyde extract phase was 4.3 wt %. About 0.5% of the formaldehyde in the original formaldehyde feed was extracted into the organic raffinate phase.

Example 9

The reactor effluent generated in Example 3, comprising 3.9 wt % sulfuric acid in crude aqueous glycolic acid, was subjected to a cross-flow batch extraction at 40° C. using an extraction solvent containing a mixture of 30 wt % tris(2-ethylhexyl)amine, 25 wt % bis(2-ethylhexyl)hydrogen phosphate and 45 wt % heptane. The extraction solvent to feed weight ratio was 1.0:1.0. The organic extract phase from this extraction was set aside and the glycolic acid-rich aqueous raffinate phase was extracted with an additional equal portion of fresh extraction solvent. This procedure was repeated two additional times with equal portions of fresh extraction solvent for a total of four cross-flow extractions. The final organic extract and aqueous raffinate phases were subjected to liquid chromatography, gas chromatography, and X-ray sulfur and phosphorus analyses to determine the compositions of the phases. None of the extractions exhibited the formation of three liquid phases. The concentration of sulfuric acid in the final aqueous raffinate phase was less than the analytical detection limit, indicating essentially 100% removal of the sulfuric acid from the hydrocarboxylation reactor effluent in four cross flow extractions.

Example 10

This example illustrates the recovery of the tertiary amine and modifier from the glycolic acid-rich aqueous raffinate phase by washing with additional diluent. The glycolic acid-rich aqueous raffinate phase from the fourth cross-flow extraction generated in Example 5, containing 1.0 wt % TEHA and 1.13 wt % DEHPA, was subjected to a cross-flow batch extraction at 40° C. using a heptane as the wash solvent. The wash solvent to aqueous feed weight ratio was 1.0:0.77. The organic wash extract from this extraction was set aside and the washed aqueous raffinate phase was extracted with an additional equal portion of fresh wash solvent. This was repeated two additional times with equal portions of fresh wash solvent for a total of four cross-flow extractions. The final organic wash extract and washed aqueous raffinate phases were subjected to gas chromatography and X-ray phosphorus analysis to determine the compositions of the phases. None of the extractions exhibited the formation of three liquid phases. The concentrations of TEHA and DEHPA in the final washed aqueous raffinate phase were 0.01 wt % and 1.03 wt %, indicating 99% and 7% recovery, respectively, in four cross flow extractions.

Example 11

This example illustrates the effect of the ratio of modifier to tertiary amine and diluent on the extraction of sulfuric acid from hydrocarboxylation reactor effluent. The reactor effluent generated in Example 3 was subjected to a series of cross-flow batch extractions at 40° C. using a extraction solvent containing 50 wt % of a mixture of tris(2-ethylhexyl) amine, 2-ethylhexanoic acid and 50 wt % of a diluent of either heptane or decane. Four cross flow extractions were completed for each extraction solvent mixture with the reactor effluent. The reactor effluent was extracted with the specified extraction solvent mixture at the given solvent to feed ratio, and the resulting aqueous raffinate phase from first extraction was contacted with a portion of fresh extraction solvent. This sequence was repeated an additional two times for a total of four cross flow extractions. The organic extract and aqueous raffinate phases from each cross flow extraction were subjected to liquid chromatography and X-ray sulfur analysis to determine the compositions of the phases. The solvent to feed conditions for each set of extractions, and the resulting sulfuric acid recovery into the extract phase, glycolic acid recovery in the raffinate, and overall molar selectivity of sulfuric acid to glycolic acid are summarized in Table 3 below.

TABLE 3

| Ex. | 2-EHA/ TEHA Wt Ratio | Diluent | S/F Extr #1 | S/F Extr #2-#4 | % $H_2SO_4$ Recov to Extract | % Glycolic Acid (GA) Recovery to Raffinate | Molar Selectivity of $H_2SO_4$ over GA |
|---|---|---|---|---|---|---|---|
| 11-1 | 1.0 | Heptane | 0.50 | 0.5 | 97.8% | 96.8% | 30.3 |
| 11-2 | 2.0 | Heptane | 0.50 | 0.16 | 94.2% | 98.0% | 46.8 |
| 11-3 | 3.0 | Heptane | 0.50 | 0.16 | 87.3% | 98.3% | 50.4 |
| 11-4 | 3.0 | Decane | 0.50 | 0.16 | 91.8% | 98.0% | 45.1 |

Example 12

This example illustrates the back extraction of sulfuric acid from the sulfuric acid-loaded organic extract phase into aqueous formaldehyde. The sulfuric acid-rich organic extract phase from the first cross-flow extraction generated in Example 11-1 contained 6.1 weight percent sulfuric acid. This mixture was subjected to cross-flow batch extractions at 75° C. using 48 wt % formaldehyde in water. The solvent to feed weight ratio in each case was 0.5:1.0. After each extraction, the aqueous formaldehyde extract was set aside and the organic raffinate phase was extracted with an additional equal portion of fresh 48 wt % aqueous formaldehyde solution. This procedure was repeated four times with equal portions of fresh solvent for a total of five cross-flow extractions. The final extract and raffinate phases were subjected to liquid chromatography and X-ray sulfur analysis to determine the compositions of the phases. None of the extractions exhibited the formation of three liquid phases. Ninety percent of the sulfuric acid in the organic extract was recovered in the aqueous formaldehyde extract phase in five cross flow extractions.

Example 13

This example illustrates the recovery of tertiary amine and modifier from the glycolic acid-rich aqueous raffinate phase by washing with additional solvents. The glycolic acid-rich aqueous raffinate phase from the fourth cross-flow extraction generated in Example 11-1 contained 2.56 wt % TEHA and 0.59 wt % 2-EHA. This mixture was divided into three parts and each part was subjected to cross-flow batch extractions at 40° C. using three different wash solvent compositions. The wash solvent to feed weight ratio in each case was 0.4:1.0. After each extraction, the organic wash extract was set aside and the washed aqueous raffinate was extracted with an additional equal portion of fresh wash solvent. This procedure was repeated three times with equal portions of fresh wash solvent for a total of four cross-flow extractions. The final organic wash extract and washed aqueous raffinate streams were subjected to gas chromatography to determine the compositions of the phases. None of the extractions exhibited the formation of three liquid phases. The concentrations and % recovery of TEHA and 2-EHA in the final washed aqueous raffinate phase are summarized in Table 4 below.

TABLE 4

| Extractant | wt % TEHA in Final Raffinate | % Recovery of TEHA | wt % 2-EHA in Final Raffinate | % Recovery of 2-EHA |
| --- | --- | --- | --- | --- |
| 100 wt % Heptane | 0.042% | 98.4% | 0.011% | 98.1% |
| 90 wt % Heptane, 10 wt % 2-Ethylhexanol | 0.018% | 99.3% | 0.000% | 100.0% |
| 90 wt % Heptane, 10 wt % n-hexanol | 0.037% | 98.6% | 0.000% | 100.0% |

Example 14

Back extraction of acid catalyst—This example illustrates the effect of modifier to tertiary amine weight ratio, percent formaldehyde, and the concentration of diluent on the back extraction of sulfuric acid from the sulfuric acid-loaded organic extract phase into aqueous formaldehyde. The sulfuric acid-rich organic extract phase from the first cross-flow extraction generated in Examples 11-2 and 11-3 were subjected to cross-flow batch extractions at 75° C. using an aqueous formaldehyde solution as the extraction solvent. The solvent to feed weight ratio in each cross flow extraction was 0.35:1.0. After each extraction, the aqueous formaldehyde extract was set aside and the organic raffinate phase was extracted with an additional equal portion of fresh aqueous formaldehyde solution. This procedure was repeated with equal portions of fresh solvent for a total of three cross-flow extractions. The final aqueous formaldehyde extract and organic raffinate phases were subjected to liquid chromatography and X-ray sulfur analysis to determine the compositions of the phases. None of the extractions exhibited the formation of three liquid phases. Feed and product specifications are given in Table 5 below.

TABLE 5

| Source of Feed | EHA/TEHA Wt Ratio in Feed | Wt % Heptane in Feed | Wt % Formaldehyde Solvent | wt % $H_2SO_4$ in Feed | % $H_2SO_4$ Extracted into Formaldehyde after Three Extractions |
| --- | --- | --- | --- | --- | --- |
| 11-2 | 2 | 50% | 48% | 4.4% | 71.4% |
| 11-2 | 2 | 50% | 35% | 4.4% | 92.2% |
| 11-2 | 2 | 50% | 20% | 4.4% | 97.1% |
| 11-2 | 2 | 50% | 0% | 4.4% | 98.6% |
| 11-2 | 2 | 67% | 48% | 4.4% | 95.6% |
| 11-2 | 2 | 67% | 35% | 4.4% | 98.9% |
| 11-2 | 2 | 67% | 20% | 4.4% | 99.2% |
| 11-2 | 2 | 67% | 0% | 4.4% | 99.3% |
| 11-3 | 3 | 50% | 48% | 3.2% | 85.3% |
| 11-3 | 3 | 50% | 35% | 3.2% | 95.3% |
| 11-3 | 3 | 50% | 20% | 3.2% | 97.9% |
| 11-3 | 3 | 50% | 0% | 3.2% | 98.8% |
| 11-3 | 3 | 67% | 48% | 3.2% | 98.3% |
| 11-3 | 3 | 67% | 35% | 3.2% | 98.8% |
| 11-3 | 3 | 67% | 20% | 3.2% | 98.9% |
| 11-3 | 3 | 67% | 0% | 3.2% | 98.9% |

Example 15

Recovery of tertiary amine and modifier—This example illustrates the recovery of tertiary amine and modifier from the glycolic acid-rich aqueous raffinate phase by washing with additional solvent. The glycolic acid-rich aqueous raffinate phases from the fourth cross-flow extraction generated in Examples 11-2, 11-3, and 11-4 were subjected to cross-flow batch extractions at 40° C. The wash solvent to feed weight ratio in each case was 0.4:1.0. After each extraction, the organic wash extract was set aside and the washed aqueous raffinate was extracted with an additional equal portion of fresh wash solvent. This procedure was repeated three times with equal portions of fresh wash solvent for a total of five cross-flow extractions. The final organic wash extract and washed aqueous raffinate streams were subjected to gas chromatography to determine the compositions of the phases. None of the extractions exhibited the formation of three liquid phases. The concentrations and % recovery of TEHA and 2-EHA in the final raffinate phases are summarized in Table 6 below.

TABLE 6

| Source of Feed | EHA/TEHA Wt Ratio in Feed | Wash Solvent | wt % TEHA in Final Raffinate | % Recov TEHA | wt % 2-EHA in Final Raffinate | % Recov 2-EHA |
| --- | --- | --- | --- | --- | --- | --- |
| 11-2 | 2 | 100 wt % Heptane | 0.230% | 84.0% | 0.018% | 96.4% |
| 11-3 | 3 | 100 wt % Heptane | 0.091% | 93.7% | 0.0% | 100.0% |
| 11-4 | 2 | 100 wt % Decane | 0.010% | 99.3% | 0.0% | 100.0% |

Example 16

This example illustrates compositions that lead to the formation of three liquid phases for an extraction solvent containing a diluent, 2-ethylhexanoic acid, and TEHA. A solution of aqueous glycolic acid and sulfuric acid was prepared by mixing crystalline glycolic acid, 98 wt % sulfuric acid, with sufficient water to give a solution containing 11.1 wt % sulfuric acid, 75.7 wt % glycolic acid, and 13.2 wt % water. This solution was contacted in a 1:1 weight ratio with mixtures containing 1:1, 2:1, and 3:1 mass ratios of 2-EHA: TEHA at 40° C., 80° C., or 100° C. The resulting mixtures separated into two liquid phases upon settling. Temperature was maintained, and an alkane diluent (either heptane or decane) was added until the onset of the formation of three liquid phases. Results are summarized in Table 7.

TABLE 7

Amount of Alkane Required to Cause Three-Phase Formation

| EHA/TEHA Mass Ratio | T (° C.) | Weight % EHA/TEHA Mix Added | Weight % Aqueous Glycolic Acid & $H_2SO_4$ Mix Added | Diluent | Weight % Alkane Added to Form Three Phases |
|---|---|---|---|---|---|
| 1.00 | 40.0 | 19.7% | 19.7% | heptane | 60.6% |
| 1.00 | 80.0 | 21.8% | 21.8% | heptane | 56.4% |
| 1.98 | 40.0 | 11.75% | 11.75% | heptane | 76.5% |
| 1.99 | 80.0 | 13.9% | 13.9% | heptane | 72.2% |
| 3.00 | 40.0 | 9.75% | 9.75% | heptane | 80.5% |
| 3.00 | 80.0 | 10.15% | 10.15% | heptane | 79.7% |
| 1.99 | 40.0 | 15.8% | 15.8% | decane | 68.4% |
| 1.99 | 100.0 | 21.8% | 21.8% | decane | 56.4% |

Example 17

Effect of diluents on 3 phase formation: This example illustrates which extraction solvent compositions lead to the formation of one, two, or three phases during the extraction of sulfuric acid from aqueous glycolic acid mixtures. A solution of 85 wt % glycolic acid in water was mixed with concentrated (98 wt %) sulfuric acid to give mixtures comprising 1%, 3%, 6%, 12%, 24%, and 33% by weight sulfuric acid in aqueous glycolic acid. Likewise, mixtures of tris(2-ethylhexyl)amine in various diluent and modifier mixtures were prepared as shown in Table 8A. The weight percentages for the diluent and modifier are for the combined diluent-modifier solution before the addition of the tertiary amine. The weight percentages of the tertiary amine indicate the weight percentage of the tertiary in the final extraction solvent composition. For example, in Example 17-1, the final extraction solvent composition contains 35 wt % TEHA and 65 wt % n-octanol. A portion of each extraction solvent was contacted with an equal mass of each of the sulfuric acid-aqueous GA mixtures in a glass vial, mixed, allowed to equilibrate, and to separate into multiple phases by holding at 40° C. or 80° C. The loss of glycolic acid into the extract phase was calculated for point one in each set of data. The sulfuric acid concentrations and the corresponding extraction are similar to equilibrium points that would be seen across a continuous countercurrent extractor. Thus, if three-phase or two-phase formation is observed in any of the samples, then such behavior most likely would occur in a continuous countercurrent extractor. The number of phases formed at each condition and the corresponding loss of glycolic acid into the amine phase at point one of each set of data is given in Table 8B. Examples 17-22 and 17-23 in Table 8B showed a 3-5 wt % loss of diluent into the aqueous glycolic acid phase.

TABLE 8A

Extraction Conditions

| Example | Temp ° C. | Wt % TEHA | Modifier | Diluent | Wt % Modifier | Wt % Diluent |
|---|---|---|---|---|---|---|
| 17-1 | 40 | 35% | n-Octanol | | 100% | |
| 17-2 | 40 | 35% | 2-ethylhexanol | | 100% | |
| 17-3 | 40 | 35.0% | 2-ethylhexanol | heptane | 50% | 50% |
| 17-4 | 40 | 34.9% | 2-ethylhexanol | heptane | 20% | 80% |
| 17-5 | 40 | 43.7% | 2-ethylhexanol | heptane | 20% | 80% |
| 17-6 | 40 | 52.3% | 2-ethylhexanol | heptane | 21% | 79% |
| 17-7 | 40 | 35% | | Heptane | | 100% |
| 17-8 | 40 | 35% | 2-heptanone | | 100% | |
| 17-9 | 40 | 35% | 2-heptanone | Heptane | 50% | 50% |
| 17-10 | 40 C. | 35% | 2-EHA | | 100% | |
| 17-11 | 40 C. | 35% | 2-EHA | Heptane | 50% | 50% |
| 17-12 | 40 C. | 35.0% | 2-EHA | heptane | 50% | 50% |
| 17-13 | 40 C. | 35.0% | 2-EHA | heptane | 20% | 80% |
| 17-14 | 40 C. | 43.8% | 2-EHA | heptane | 20% | 80% |
| 17-15 | 40 C. | 52.4% | 2-EHA | heptane | 20% | 80% |
| 17-16 | 40 C. | 35% | Lauric acid | | 100% | |
| 17-17 | 40 C. | 35% | Dibutyl Ether | | 100% | |
| 17-18 | 40 C. | 35% | | Toluene | | 100% |
| 17-19 | 40 C. | 52.5% | 2-EHA | Heptane | 50% | 50% |
| 17-20 | 40 C. | 17.5% | 2-EHA | Heptane | 50% | 50% |
| 17-21 | 40 C. | 35.0% | 5-ethyl-2-nonanone | | 100% | |
| 17-22 | 40 C. | 34.8% | 5-ethyl-2-nonanone | heptane | 50% | 50% |
| 17-23 | 40 C. | 35.0% | 5-ethyl-2-nonanone | heptane | 20% | 80% |
| 17-24 | 40 C. | 21.3% | 2-EHA | Heptane | 50% | 50% |
| 17-25 | 40 C. | 21.3% | n-Decanol | Heptane | 50% | 50% |

TABLE 8B

Results of Extraction

| | Number of Phases Present After Extraction | | | | | | % GA Loss |
|---|---|---|---|---|---|---|---|
| Example | Point 1—1% $H_2SO_4$ | Point 2—3% $H_2SO_4$ | Point 3—6% $H_2SO_4$ | Point 4—12% $H_2SO_4$ | Point 5—24% $H_2SO_4$ | Point 6—33% $H_2SO_4$ | to Amine Phase at Point 1 |
| 17-1 | 1 | 1 | 2 | 2 | | | 100% |
| 17-2 | 2 | 2 | 2 | 2 | | | 15% |
| 17-3 | 2 | 3 | 3 | 2 | 2 | 2 | 9.2% |
| 17-4 | 2 | 3 | 3 | 3 | 3 | 3 | 3.4% |
| 17-5 | 2 | 3 | 3 | 3 | 3 | 3 | 3.2% |
| 17-6 | 2 | 2 | 3 | 3 | 3 | 3 | 0% |
| 17-7 | 2 | 3 | 3 | 3 | | | 0% |
| 17-8 | 1 | 1 | 1 | 2 | | | 100% |

TABLE 8B-continued

Results of Extraction

| Example | Number of Phases Present After Extraction | | | | | | % GA Loss to Amine Phase at Point 1 |
|---|---|---|---|---|---|---|---|
| | Point 1—1% $H_2SO_4$ | Point 2—3% $H_2SO_4$ | Point 3—6% $H_2SO_4$ | Point 4—12% $H_2SO_4$ | Point 5—24% $H_2SO_4$ | Point 6—33% $H_2SO_4$ | |
| 17-9 | 2 | 3 | 3 | 3 | | | 10% |
| 17-10 | 2 | 2 | 2 | 2 | 2 | 2 | 13% |
| 17-11 | 2 | 2 | 2 | 2 | 2 | 2 | 0% |
| 17-12 | 2 | 2 | 2 | 2 | 2 | 2 | 4.2% |
| 17-13 | 2 | 2 | 3 | 3 | 3 | 3 | 0.5% |
| 17-14 | 2 | 2 | 3 | 3 | 3 | 3 | 0.7% |
| 17-15 | 2 | 2 | 3 | 3 | 3 | 3 | 0% |
| 17-16 | 2 | 2 | 2 | 2 | | | 0% |
| 17-17 | 2 | 3 | 3 | 3 | | | 32% |
| 17-18 | 2 | 3 | 3 | 3 | | | 0% |
| 17-19 | 2 | 2 | 2 | 2 | 2 | 2 | 0% |
| 17-20 | 2 | 2 | 2 | 2 | 2 | 2 | 0% |
| 17-21 | 2 | 2 | 2 | 2 | 2 | 2 | 5% |
| 17-22 | 2 | 2 | 3 | 3 | 3 | 3 | 3-5% |
| 17-23 | 2 | 2 | 3 | 3 | 3 | 3 | 3-5% |
| 17-24 | 2 | 2 | 2 | 2 | 2 | 2 | 0% |

Example 18

Extraction of methanetrisulfonic acid—This example illustrates the effect of the ratio of modifier to tertiary amine for the extraction of methanetrisulfonic acid ("MTSA") from hydrocarboxylation reactor effluent. The aqueous reactor effluent generated in Example 4 was subjected to a series of cross-flow batch extractions at 40° C. using a extraction solvent containing 50 wt % of a mixture of tris(2-ethylhexyl) amine, 2-ethylhexanoic acid and 50 wt % heptane as a diluent. Three cross flow extractions were completed for each extraction solvent mixture with the reactor effluent. The reactor effluent was extracted with the specified extraction solvent mixture and the resulting aqueous glycolic acid phase from first extraction was contacted with a portion of fresh extraction solvent. This sequence was repeated an additional time for a total of three cross flow extractions. The solvent to feed ratio was 0.5:1 in the first extraction and 0.16:1 for extractions 2-4. The organic extract and aqueous raffinate phases from each cross flow extraction were subjected to liquid chromatography and X-ray sulfur analysis to determine the compositions of the phases. The feed conditions for each set of extractions, and the resulting MTSA recovery into the organic extract phase, glycolic acid recovery in the aqueous raffinate, and overall molar selectivity of MTSA to glycolic acid are summarized in Table 9 below.

TABLE 9

| Example | EHA/TEHA Wt Ratio | % Diluent | % MTSA Recov to Extract | % Glycolic Acid (GA) Recovery to Raffinate | Molar Selectivity of MTSA over GA |
|---|---|---|---|---|---|
| 18-1 | 3.0 | 50% | 96.2% | 98.5% | 65.0 |
| 18-2 | 2.0 | 50% | 97.4% | 99.0% | 101.0 |

Example 19

Back extraction of methanetrisulfonic acid—This example illustrates the effect of modifier to tertiary amine weight ratio and concentration of diluent on the back extraction of methanetrisulfonic acid from the MTSA-loaded organic extract phase into aqueous formaldehyde. The MTSA-rich extract phase from the first cross-flow extraction generated in Example 18-2 was subjected to cross-flow batch extractions at 75° C. using an aqueous formaldehyde solution as the extraction solvent at the solvent to feed ratio indicated in Table 10. After each extraction, the organic extract phase was set aside and the aqueous raffinate phase was extracted with an additional equal portion of fresh aqueous formaldehyde solution. This procedure was repeated with equal portions of fresh solvent for a total of three cross-flow extractions. The final extract and raffinate phases were subjected to liquid chromatography and X-ray sulfur analysis to determine the compositions of the phases. None of the extractions exhibited the formation of three liquid phases. Feed and product specifications are given in Table 10 below.

TABLE 10

| Source of Feed | EHA/TEHA Wt Ratio Feed | Wt % Heptane in Feed | Wt % Formaldehyde Solvent | wt % $H_2SO_4$ in Feed | S/F Ratio | % MTSA Extracted into Formaldehyde Phase after 3 Extractions |
|---|---|---|---|---|---|---|
| 18-2 | 2 | 50% | 38.5% | 3.41% | 0.35 | 50.1% |
| 18-2 | 2 | 50% | 28.1% | 3.41% | 0.35 | 67.2% |
| 18-2 | 2 | 50% | 16.0% | 3.41% | 0.35 | 86.5% |
| 18-2 | 2 | 50% | 0.0% | 3.41% | 0.35 | 92.0% |
| 18-2 | 2 | 67% | 38.5% | 3.41% | 0.23 | 80.8% |
| 18-2 | 2 | 67% | 28.1% | 3.41% | 0.23 | 90.4% |
| 18-2 | 2 | 67% | 16.0% | 3.41% | 0.23 | 93.1% |
| 18-2 | 2 | 67% | 0.0% | 3.41% | 0.23 | 95.5% |

Example 20

Recovery of tertiary amine and modifier from aqueous raffinate—This example illustrates the recovery of the tertiary amine and modifier from the glycolic acid-rich aqueous raffinate phase by washing with additional solvent. The glycolic acid-rich raffinate phase from the fourth cross-flow extraction generated in Examples 14-1 and 14-2 were combined and subjected to cross-flow batch extractions at 40° C. The combined glycolic acid rich, raffinate phases contained 0.43 wt % TEHA and 0.39 wt % 2-ethylhexanoic acid. The solvent to feed weight ratio in each case was 0.4:1.0. After each extraction, the organic wash extract was set aside and the washed aqueous raffinate was extracted with an additional equal portion of fresh wash solvent. This procedure was repeated four more times with equal portions of fresh wash solvent for a total of six cross-flow extractions. The final organic wash extract and washed aqueous raffinate phases were subjected to gas chromatography to determine the compositions of the phases. None of the extractions exhibited the formation of three liquid phases. The concentrations and % recovery of TEHA and 2-EHA in the final raffinate phases are summarized in Table 11 below.

TABLE 11

| Source of Feed | Wash Solvent | wt % TEHA in Final Raffinate | % Recovery of TEHA | wt % 2-EHA in Final Raffinate | % Recovery of 2-EHA |
|---|---|---|---|---|---|
| 18-1, -2 | 100 wt % Heptane | 0.038% | 92.0% | None detected | 100.0% |

Example 21

Extraction of trifluoromethanesulfonic acid (triflic acid)—This example illustrates the effect of the ratio of modifier to tertiary amine and diluent concentration on the extraction of triflic acid from aqueous glycolic acid. A mixture comprising 82.4 wt % glycolic acid, 14.6 wt % water, and 3.0 wt % triflic acid was subjected to a cross-flow batch extraction at 40° C. using two different extraction solvents containing a mixture of tris(2-ethylhexyl)amine, 2-ethylhexanoic acid, and heptane as diluent. Extraction conditions and results are given below in Table 12.

TABLE 12

| Example | Solvent EHA/TEHA Wt Ratio | Wt % TEHA | Wt % 2-EHA | Wt % Heptane | Solvent/Feed Weight Ratio | % Triflic Recov to Extract |
|---|---|---|---|---|---|---|
| 21-1 | 3.0 | 12.4% | 37.3% | 50.3% | 1.45 | 99.4% |
| 21-2 | 2.9 | 8.4% | 24.8% | 66.2% | 1.50 | 98.3% |

Example 22

Back extraction of triflic acid—This example illustrates the effect of modifier to tertiary amine weight ratio and concentration of diluent on the back extraction of triflic acid from the triflic acid-loaded organic extract phase into aqueous formaldehyde solution. The triflic acid-rich, organic extract phases from the cross-flow extractions generated in Examples 21-1 and 21-2 were subjected to cross-flow batch extractions at 70° C. using aqueous formaldehyde as the extraction solvent at the solvent to feed ratio shown in Table 13. After each extraction, the aqueous formaldehyde extract was set aside and the organic raffinate phase was extracted with an additional equal portion of fresh aqueous formaldehyde solution. This procedure was repeated with equal portions of fresh solvent for a total of five cross-flow extractions. The final aqueous formaldehyde extract and organic raffinate streams were subjected to liquid chromatography and X-ray sulfur analysis to determine the compositions of the phases. None of the extractions exhibited the formation of three liquid phases. Feed and product specifications are given in Table 13 below.

TABLE 13

| Source of Feed | EHA/TEHA Wt Ratio Feed | Wt % Heptane in Feed | Wt % Formaldehyde in Solvent | wt % Triflic in Feed | S/F Ratio | % Triflic Extracted into Solvent Phase after Three Extractions |
|---|---|---|---|---|---|---|
| 21-1 | 3.0 | 50.3% | 0% | 2.00% | 0.5 | 62.2% |
| 21-2 | 2.9 | 66.2% | 0% | 1.90% | 0.5 | 94.8% |
| 21-1 | 3.0 | 50.3% | 51.0% | 2.2% | 1.0 | 39.8% |
| 21-2 | 2.9 | 66.2% | 51.0% | 2.00% | 1.0 | 69.3% |

Examples 23-35

Triflic Acid Extract with Perfluorooctanoic Acid Modifier—Cross-flow ("forward") extractions were performed at 70° C. using 85 wt % or 95 wt % aqueous glycolic acid, an equal weight of heptane phase comprising 25-50 wt % heptane, tris(2-ethylhexyl)amine ("TEHA") and perfluorooctanoic acid ("PFOAH") (1.5-3.0 eq PFOAH:eq TEHA), and a variety of initial triflic acid loadings (0.025-4.0 eq:eq TEHA). Back ("reverse") extractions were performed under similar conditions using 50 wt % aqueous formaldehyde. The triflic acid concentrations were determined by sampling both phases and analyzing the samples by x-ray fluorescence (XRF) or inductively-coupled plasma (ICP), using standard methods known in the art and are shown in Tables 14-15

Representative procedures for the forward and back extractions Trifluoromethanesulfonic acid (TfOH), perfluorooctanoic acid (PFOA-H) and 95% paraformaldehyde (HFr) were obtained from Sigma-Aldrich, tris(2-ethylhexyl)amine from TCI America, and GLYPURE™ glycolic acid from DuPont.

Example 23

Preparation of 95% Aqueous Glycolic acid solution—Glycolic acid (23.69 g) was combined with water (1.23 g) and warmed with stirring to 85° C. forming a clear, viscous solution. The solution was stable upon cooling to 70° C. over the time frame of the experiments.

Example 24

Preparation of [TEHA-PFOA] for Forward Extraction—Perfluorooctanoic acid (38.165 g, 92.17 mmol) was combined with tris(2-ethylhexyl)amine (16.48 g, 46.58 mmol) and heptanes (18.02 g), and warmed with stirring to 70° C. to form a clear, pink solution comprising 0.641 mol salt/kg and 0.627 mol free PFOA-H/kg.

Example 25

Preparation of [TEHA-PFOA]salt solution for Back Extraction—Perfluorooctanoic acid (24.466 g, 63.92 mmol) was combined with tris(2-ethylhexyl)amine (11.26 g, 31.96 mmol) and heptanes (37.73 g), and warmed with stirring to 70° C. to form a clear, pink solution comprising 0.424 mol salt/kg and 0.424 mol free PFOA-H/kg.

Example 26

Preparation of 50% Aqueous Formaldehyde solution—Paraformaldehyde (49.964 g), water (45.331 g) and trifluoromethanesulfonic acid (93 mg, 0.620 mmol) were combined and stirred at 97° C. for 48 h. The solution remained homogeneous upon cooling to 70° C.

Examples 27-30

Forward Extraction of Trifluoromethanesulfonic Acid—A typical procedure for the forward extraction follows: Glycolic acid solution (10.928 g) was added to a vial followed by TfOH (993 mg, 6.62 mmol) and [TEHA-PFOA] salt solution (10.999 g, 7.051 mmol salt), all at 70° C. Examples 27-29 used an 85 wt % aqueous glycolic acid while Examples 29 and 30 used 95 wt % aqueous glycolic acid; the remaining examples used 85 wt % aqueous glycolic acid. The contents of the vial were thoroughly agitated, centrifuged, and allowed to separate into an upper organic layer and a lower aqueous layer. Each layer was sampled for XRF or ICP analysis for sulfur content. The aqueous layer was removed with a Pasteur pipette, added to a new vial, and weighed. The TfOH/glycolic acid solution was then repeatedly extracted by adding an equal weight of fresh salt solution to the raffinate layer and repeating the above steps. The results are shown in Table 14.

Examples 31-35

Back Extractions of Trifluoromethane Sulfonic Acid—A typical procedure for the back extraction of triflic acid from a solution of TEHA and PFOA in heptane follows: [TEHA-PFOA] salt solution (4.266 g, 1.81 mmol salt) was combined with TfOH (237 mg, 1.62 mmol) and 50% aqueous HFr (4.108 g), all at 70° C., in a vial, simulating the back extraction at a high level of TfOH loading. The contents of the vial were thoroughly agitated, centrifuged, and allowed to separate into an upper organic layer and a lower aqueous layer. Each layer was sampled for XRF or ICP analysis for sulfur content. Samples of the aqueous HFr layer were added to vials containing pre-weighed isopropanol to avoid precipitation of HFr upon cooling. The steps above were repeated for each back extraction by combining [TEHA-PFOA] salt solution, TfOH and 50% aqueous HFr in vials such that TfOH was loaded at 0.5, 0.25, 0.125, 0.05 and 0.025 equivalent to 1 equivalent salt. The results are shown in Table 15.

TABLE 14

Forward Extractions of Triflic Acid with PFOA

| Ex | Excess PFOA (equiv) | Dil. wt % | Phase | Extraction stage, wt % Triflic acid | | | | | | |
|---|---|---|---|---|---|---|---|---|---|---|
| | | | | 1 | 2 | 3 | 4 | 5 | 6 | 7 |
| 27 | 1.0 | 50 | Aq | 2.881 | 1.618 | 0.727 | 0.334 | 0.113 | 0.051 | 0.020 |
| | | | Org | 2.856 | 1.743 | 0.965 | 0.461 | 0.174 | 0.071 | 0.027 |
| 28 | 1.0 | 25 | Aq | 4.405 | 1.754 | 0.588 | 0.141 | 0.040 | 0.011 | 0.008 |
| | | | Org | 4.486 | 2.745 | 1.308 | 0.460 | 0.116 | 0.015 | 0.004 |
| 29 | 0.5 | 25 | Aq | 2.292 | 0.207 | — | — | — | — | — |
| | | | Org | 7.017 | 2.250 | — | — | — | — | — |
| 30 | 1 | 25 | Aq | 3.182 | 0.781 | 0.089 | 0.010 | — | — | — |
| | | | Org | 5.569 | 2.634 | 0.671 | 0.098 | — | — | — |

TABLE 15

Back Extractions of Triflic Acid with PFOA

| Ex | Excess PFOA (equiv) | Dil. wt % | Phase | Extraction stage, wt % Triflic acid | | | | | |
|---|---|---|---|---|---|---|---|---|---|
| | | | | 1 | 2 | 3 | 4 | 5 | 6 |
| 31 | 1.0 | 50 | Aq | 0.219 | 0.111 | 0.111 | 0.096 | — | — |
| | | | Org | 0.041 | 0.028 | 0.014 | 0.016 | — | — |
| 32 | 1.0 | 50 | Aq | 3.452 | 2.076 | 1.131 | 0.935 | — | — |
| | | | Org | 0.922 | 0.539 | 0.257 | 0.152 | — | — |
| 33 | 1.0 | 25 | Aq | 6.748 | 3.588 | 1.871 | 0.971 | — | — |
| | | | Org | 2.147 | 1.262 | 0.687 | 0.317 | — | — |
| 34 | 2.0 | 50 | Aq | 13.933 | 9.395 | 4.752 | 2.724 | — | — |
| | | | Org | 1.504 | 0.554 | 0.146 | 0.066 | — | — |
| 35 | 1.0 | 50 | Aq | 4.868 | 2.527 | 1.444 | 0.787 | 0.365 | 0.197 |
| | | | Org | 1.105 | 0.636 | 0.356 | 0.162 | 0.089 | 0.045 |

Examples 36-40

Forward Extractions of Sulfuric Acid in Continuous Column—For examples 36 through 48, continuous extraction experiments were carried out in a Karr column containing four jacketed glass column sections (15.9 mm inside diameter, each 501 mm in length) stacked on top of each other. Jacketed glass disengagement sections, 25.4 mm inside diameter and 200 mm in length, were attached to the top and bottom of the four extractor sections. The four column sections and two disengagement sections were joined together with TEFLON™ O-ring gaskets (25 mm thickness) held together with bolted flanges to form the column body. Feed ports were fitted into each TEFLON™ O-ring to allow change of feed locations. The total height of the resulting column was approximately 2.6 meters. Separate temperature-controlled heating baths were connected to the jacket of each disengagement zone and one bath to the combined four column sections to maintain the desired extraction temperature gradient.

Agitation in the column was supplied by an 3.2 mm diameter Hastelloy 276C impeller shaft fitted with seventy-seven TEFLON™ plates, each with eight radial rectangular petals (to provide gaps for liquid flow paths), spaced 25 mm apart in the column sections. The impeller shaft was attached at the top of the extractor to an electric motor fitted with a concentric gear to convert rotational motion into reciprocal motion. The agitator stroke length (i.e., extent of vertical motion) was 19 mm, and varied from 200 to 350 strokes per minute.

Depending on the chosen continuous phase, the liquid-liquid phase interface was maintained in either the top or bottom disengagement section (in the top section if the less dense phase were continuous, bottom section if the more dense phase were continuous) by visual observation and manual manipulation of the underflow take-off pump.

Up to three feeds could be supplied to the column via piston pumps from independently temperature-controlled jacketed glass vessels of four liter, two liter, and two liter volumes, while the underflow (more dense) product and the top, overflow (less dense) product were collected in two-liter glass vessels. The top product collected by gravity overflow from the upper disengagement section, while the bottoms product flow was controlled by a variable rate piston pump.

For the following examples possible feed locations are designated as follows from the top of the column to the bottom:

F1: Feed location between top disengagement zone and 1st column section
F2: Feed location between $1^{st}$ and $2^{nd}$ column sections
F3: Feed location between $2^{nd}$ and $3^{rd}$ column sections
F4: Feed location between $3^{rd}$ and $4^{th}$ column sections
F5: Feed location between $4^{th}$ column section and bottom disengagement zone Hydrocarboxylation reactor effluents containing sulfuric acid, glycolic acid, glycolate oligomers, and water were fed to the continuous Karr column described above and contacted with an extraction solvent comprising an amine, carboxylic acid, and hydrocarbon diluent, and optionally a wash solvent. The column was operated with the solvent as the continuous phase. Feed, solvent, and wash compositions, flow rates, feed locations, and temperature of the forward extraction experiments are summarized in Table 16. In each experiment, the column reached steady state within an hour and was run continuously for six to eight hours, with sampling occurring every one to two hours. Averaged recoveries of glycolate species, amine, carboxylic acid, and hydrocarbon to the raffinate product, and sulfuric acid to the extract product over the time of steady state operation are given in Table 17.

TABLE 16

Feed Conditions for Forward Extractions of Sulfuric Acid in Continuous Karr Column Operation

| Ex | T, °C. | Agit. Rate Strokes/ min | Mass S/F Ratio | Feed Flow g/min | Feed Location | wt % $H_2SO_4$ | wt % GA Oligomers | wt % Water |
|---|---|---|---|---|---|---|---|---|
| 36 | 70 | 350 | 1.14 | 13.3 | F1 | 3.43% | 82.2% | 14.33% |
| 37 | 70 | 325 | 1.14 | 13.3 | F1 | 2.99% | 72.9% | 24.16% |
| 38 | 45 | 325 | 1.13 | 13.3 | F1 | 2.93% | 82.8% | 14.30% |
| 39 | 40 | 206 | 1.13 | 13.3 | F1 | 4.14% | 79.1% | 16.72% |
| 40 | 45 | 300 | 0.76 | 13.3 | F1 | 0.78% | 82.5% | 16.72% |

| Ex. | Solv. Flow g/min | Solvent Location | Solv. Comp. TEHA | 2-EHA | Heptane | Wash Flow mL/ min | Wash Location | Wash Comp Heptane |
|---|---|---|---|---|---|---|---|---|
| 36 | 15.2 | F5 | 10.11% | 36.49% | 53.40% | none | | |
| 37 | 15.2 | F4 | 10.78% | 37.39% | 51.83% | 6.9 | F5 | 100.0% |
| 38 | 15.2 | F4 | 9.99% | 36.96% | 53.05% | 6.9 | F5 | 100.0% |
| 39 | 15.2 | F5 | 10.00% | 36.13% | 53.87% | none | | |
| 40 | 11.4 | F5 | 10.73% | 36.50% | 52.77% | none | | |

TABLE 17

Results of Forward Extractions of Sulfuric Acid in Continuous Karr Column Operation

| Ex. | TEHA/ $H_2SO_4$ molar ratio | EHA/ TEHA molar ratio | $H_2SO_4$ | Amine | Heptane | 2-EHA | Glycolic Oligomers |
|---|---|---|---|---|---|---|---|
| 36 | 0.94 | 3.61 | 98.6% | 97.7% | 100.0% | 99.3% | 99.1% |
| 37 | 1.14 | 3.47 | 99.3% | 98.6% | 100.0% | 99.6% | 98.9% |
| 38 | 1.08 | 3.70 | 97.8% | 98.4% | 100.0% | 98.8% | 98.8% |
| 39 | 0.76 | 3.61 | 80.3% | 98.9% | 100.0% | 99.0% | 99.0% |
| 40 | 3.26 | 3.40 | 93.4% | 90.0% | 100.0% | 97.0% | 99.5% |

Examples 41-42

Continuous Wash of Raffinate from Forward Extraction—For example 41, the sulfuric acid-lean raffinate of Example 36, comprising glycolic acid, glycolate oligomers, and water was contacted continuously with a heptane wash solvent as the continuous phase in the Karr column described above to remove additional 2-ethylhexanoic acid and TEHA. Similarly for Example 42, the raffinate from Example 39 was contacted with heptane in the continuous column to remove additional 2-ethylhexanoic acid and TEHA. Feed compositions, flow rates, feed locations, and temperature of the wash experiments are summarized in Table 18. In each experiment, the column reached steady state within an hour and was run continuously for six to eight hours, with sampling occurring every one to two hours. Averaged recoveries of TEHA, 2-ethylhexanoic acid, and heptane to wash extract product over the time of steady state operation are given in Table 19.

TABLE 18

Feed Conditions for Wash Extractions of Raffinates from Continuous Forward Extractions

| Ex. | T, °C. | Agit Rate Strokes/min | Mass W/F Ratio | Feed Flow g/min | Feed Location | wt % TEHA | wt % 2-EHA | Wash Flow g/min | Wash Location |
|---|---|---|---|---|---|---|---|---|---|
| 41 | 45 | 200 | 0.52 | 13.3 | F1 | 0.17% | 0.46% | 6.9 | F5 |
| 42 | 70 | 310 | 0.51 | 20.0 | F1 | 0.62% | 0.8% | 6.9 | F5 |

TABLE 19

Results of Wash Extractions of Raffinates from Continuous Forward Extractions

| Ex. | Amine | Heptane | 2-EHA |
|---|---|---|---|
| 41 | 91.6% | 99.97% | 93.1% |
| 42 | 87.0% | 99.9% | 82.7% |

Examples 43-48

Back Extractions of Sulfuric Acid-Rich Solvents in Continuous Column—Sulfuric acid-rich extracts comprising sulfuric acid, TEHA, 2-ethylhexanoic acid, and heptane derived from the forward extraction of hydrocarboxylation effluents were fed to the continuous Karr column at a temperature of 70° C. as described above and contacted with an aqueous formaldehyde extraction solvent (continuous phase). The sulfuric acid-rich extracts were introduced to the Karr column at location F5 and the aqueous formaldehyde solvent was introduced at location F1. Feed and solvent compositions, and flow rates of the forward extraction experiments are summarized in Table 20. In each experiment, the column reached steady state within an hour and was run continuously for six to eight hours, with sampling occurring every one to two hours. Averaged recoveries of TEHA, 2-ethylhexanoic acid, and heptane to the raffinate product, and glycolic acid and sulfuric acid to the formaldehyde extract product over the time of steady state operation are given in Table 21.

TABLE 20

Feed Conditions for Continuous Back Extractions with Aqueous Formaldehyde

| Ex. | Feed | Agit. Rate Strokes/min | Mass S/F Ratio | Feed Flow g/min | Feed Wt % H₂SO₄ | GA Olig. |
|---|---|---|---|---|---|---|
| 43 | sulfuric acid-rich extract | 310 | 1.45 | 11.4 | 2.59% | 0.93% |
| 44 | Extract Example 36 | 310 | 2.76 | 11.4 | 2.21% | 0.45% |
| 45 | Extract Example 37 | 300 | 2.89 | 7.6 | 1.99% | 0.49% |
| 46 | Extract Example 37 | 327 | 2.23 | 7.6 | 1.99% | 0.49% |
| 47 | Extract Example 37 | 327 | 1.49 | 7.6 | 1.99% | 0.49% |
| 48 | Extract Example 38 | 332 | 0.495 | 22.8 | 1.87% | 0.51% |

TABLE 20-continued

Feed Conditions for Continuous Back Extractions with Aqueous Formaldehyde

| Ex. | TEHA | 2-EHA | Heptane | Solvent Flow g/min | Solv. wt % (aq. HFr) | water |
|---|---|---|---|---|---|---|
| 43 | 9.33% | 36.5% | 50.65% | 16.5 | 49.00% | 51% |
| 44 | 7.38% | 29.1% | 60.89% | 31.5 | 45.00% | 55% |
| 45 | 7.54% | 26.3% | 63.71% | 22.0 | 42.00% | 58% |
| 46 | 7.54% | 26.3% | 63.71% | 17.0 | 49.00% | 51% |
| 47 | 7.54% | 26.3% | 63.71% | 11.3 | 42.00% | 58% |
| 48 | 7.41% | 27.7% | 62.49% | 11.3 | 49.90% | 50.1% |

TABLE 21

Results for Continuous Back Extractions with Aqueous Formaldehyde

| | Recovery to Formaldehyde Extract Product | | Recovery to Raffinate Product | | |
|---|---|---|---|---|---|
| Ex. | H2SO4 | Glycolic Oligomers | Amine | Heptane | 2-EHA |
| 43 | 98.4% | 100.0% | 98.8% | 100.0% | 95.3% |
| 44 | 99.8% | 100.0% | 99.0% | 100.0% | 100.0% |
| 45 | 99.4% | 100.0% | 100.0% | 100.0% | 94.7% |
| 46 | 98.8% | 100.0% | 98.0% | 100.0% | 94.4% |
| 47 | 98.8% | 100.0% | 98.0% | 100.0% | 94.4% |
| 48 | 98.7% | 99.8% | | 100.0% | 99.5% |

Example 49

Extraction of Sulfuric Acid from Aqueous Glycolic Acid—Sulfuric acid was added to a 85 wt % glycolic acid-15 wt % water mixture to produce a solution comprising 3 wt % sulfuric acid. Extraction solvents were prepared by mixing an amine and diluents(s) as specified in Table 22. Five grams of each amine solvent solution was mixed with five grams of the sulfuric acid-aqueous glycolic acid mixture and allowed equilibrate at the temperature specified in Table 22. If two phases resulted, samples of each phase were analyzed by x-ray for sulfur content and converted into a sulfuric acid concentration in each phase (grams of sulfuric acid per gram of amine phase and grams of sulfuric acid per gram of aqueous glycolic acid phase).

TABLE 22

Extraction of Sulfuric Acid from Aqueous Glycolic Acid

| Amine | Diluent 1 | Diluent 2 | Wt % Amine | Wt % D1 | Wt % D2 | T, ° C. | Phases | Acid/GA | Acid/Amine |
|---|---|---|---|---|---|---|---|---|---|
| TEHA | n-Octanol | none | 35% | 65% | 0% | 40 | 1 | n/a | |
| TEHA | 2-Ethylhexanol | none | 35% | 65% | 0% | 40 | 2 | 0.0012 | 0.0290 |
| TEHA | Heptane | none | 35% | 65% | 0% | 40 | 2 | 0.0132 | 0.0125 |
| TEHA | 2-Heptanone | none | 35% | 65% | 0% | 40 | 1 | n/a | |
| Alamine 336 | n-Octanol | none | 35% | 65% | 0% | 40 | 2 | 0.0004 | 0.0286 |
| Alamine 336 | 2-Ethylhexanol | none | 35% | 65% | 0% | 40 | 2 | 0.0006 | 0.0290 |
| Alamine 336 | Heptane | none | 35% | 65% | 0% | 40 | 3 | n/a | |
| Alamine 336 | 2-Heptanone | none | 35% | 65% | 0% | 40 | 2 | 0.0003 | 0.0288 |
| TEHA | 2-EHA | none | 35% | 65% | 0% | 40 | 2 | 0.0012 | 0.0260 |

TABLE 22-continued

Extraction of Sulfuric Acid from Aqueous Glycolic Acid

| Amine | Diluent 1 | Diluent 2 | Wt % Amine | Wt % D1 | Wt % D2 | T, °C. | Phases | Acid/ GA | Acid/ Amine |
|---|---|---|---|---|---|---|---|---|---|
| TEHA | 2-EHA | Heptane | 35% | 32.5% | 32% | 40 | 2 | 0.0019 | 0.0264 |
| TEHA | Lauric acid | none | 35% | 65% | 0% | 40 | 2 | 0.0011 | 0.0244 |
| TEHA | 2-Heptanone | Heptane | 35% | 32.5% | 32% | 40 | 3 | n/a | |
| TEHA | Dibutylether | none | 35% | 65% | 0% | 40 | 3 | n/a | |
| TEHA | Toluene | none | 35% | 65% | 0% | 40 | 3 | n/a | |
| Alamine 336 | 2-EHA | none | 35% | 65% | 0% | 40 | 2 | 0.0005 | 0.0276 |
| Alamine 336 | Toluene | none | 35% | 65% | 0% | 40 | 2 | 0.0001 | 0.0278 |
| TEHA | 2-EHA | none | 35% | 65% | 0% | 80 | 2 | 0.0017 | 0.0282 |
| TEHA | 2-EHA | Heptane | 35% | 32.5% | 32% | 80 | 2 | 0.0055 | 0.0230 |
| TEHA | Lauric acid | none | 35% | 65% | 0% | 80 | 2 | 0.0018 | 0.0198 |
| TEHA | 2-Heptanone | Heptane | 35% | 32.5% | 32% | 80 | 3 | n/a | |
| TEHA | Dibutylether | none | 35% | 65% | 0% | 80 | 3 | n/a | |
| TEHA | Toluene | none | 35% | 65% | 0% | 80 | 3 | n/a | |
| Alamine 336 | 2-EHA | none | 35% | 65% | 0% | 80 | 2 | 0.0004 | 0.0281 |
| Alamine 336 | Toluene | none | 35% | 65% | 0% | 80 | 2 | 0.0001 | 0.0283 |

General: Preparation of Glycolic Acid with Sulfonated Strong Acid Catalysts

Examples 50-53, 55-61 and Comparative Examples 54, 62-67

Sulfuric acid was purchased from J. T. Baker and used as received. Methanedisulfonic acid ("MDSA"), methanetrisulfonic acid ("MTSA"), bis(methanesulfonyl)methanesulfonic acid ("BMMSA") and methanesulfonylmethanesulfonic acid ("MMSA") were prepared as described in Examples 50-53 below. Formaldehyde (approximately 95 weight percent as paraformaldehyde prills) and glycolic acid (99+%—Glypure®) were purchased from Aldrich Chemical Co. and used as received. Fuming sulfuric acid was purchased from Alfa Aesar and used as received.

All batch hydrocarboxylation reaction experiments were completed using a reactor system comprising a 100 mL zirconium autoclave. The high pressure autoclave was fitted with an impeller, gas inlet tube, sample tube, and thermowell. The autoclave was heated electrically by a band heater, with temperature control provided by feedback via a thermocouple in the autoclave thermowell. Pure carbon monoxide gas (>99.9%) was fed to the autoclave via a high pressure flow controller. The catalyst, formaldehyde, water, and glycolic acid were added to the autoclave, the autoclave was sealed, and purged with CO. The initial rate of reaction for glycolic acid formation in the hydrocarboxylation of HCHO was compared for the following acid catalysts; $H_2SO_4$, MDSA, MTSA, MMSA, and BMMSA. Each reaction was run for four hours under 69 bars gauge (1000 psig) CO at 140° C. with a HCHO:GA:$H_2O$ mole loading of 1:2:1.4.

As described above, the analysis of reaction products comprising glycolic acid, glycolate oligomers and esters, and related species (e.g., diglycolic acid and esters, methoxy acetic acid and esters, etc.) for both batch and continuous reaction experiments was performed using ion-exclusion chromatography after reaction product samples were subjected to acid hydrolysis in aqueous 25% v/v $H_2SO_4$ at 80° C. for 30 minutes. Reaction products that produce glycolic acid upon hydrolysis, therefore, are reported below as glycolic acid. Formaldehyde was analyzed as described above. The temperature and pressure were maintained throughout the reaction and samples of the reaction mixture were taken periodically to follow its progress by HPLC.

All continuous hydrocarboxylation reaction experiments were completed using a reactor system comprising a Hastelloy autoclave with a 125 mL nominal volume, and the associated feed and product storage equipment. The high pressure autoclave was fitted with a hollow shaft Rushton turbine impeller (for gas introduction and dispersion), baffles, thermowell, gas inlet tube, and sip tube to maintain liquid level at approximately 90 mL and to provide an exit for product effluent. The autoclave was heated electrically by a band heater, with temperature control provided by feedback via a K-type thermocouple in the autoclave thermowell.

Pure carbon monoxide gas (>99.9 volume %) was fed to the autoclave via a high pressure flow controller. The gas entered the body of the autoclave via grooves in the impeller bearings. The off-gas flow rates were monitored by a dry bubble-type flow meter. Liquid feed flow rate was controlled to a precision of 0.001 mL/min by one or two double-barreled 500 ml high precision syringe pumps connected to stirred feed vessels (either stainless steel or glass). The glass vessels were jacketed and could be heated or cooled. Generally both the catalyst and feed components were fed together from an unheated vessel.

Reactor effluent passed through heated Hastelloy tubing, an automatic pressure control valve (research control valve), and into heatable Hastelloy collection vessels (1 liter). The effluent collection vessel was fitted with a chilled coiled condenser. The gas outlet from the effluent tank was connected to a manual back pressure regulator to maintain vessel pressure at 2.76-6.89 bars gauge (40-100 psig). Temperatures, pressures, and other relevant system parameters were recorded automatically by a distributed control system.

Example 50

Preparation of Methanedisulfonic Acid—PUROLITE™ C-100×10 ion exchange resin (1100 grams, 1600 mL) was charged equally to two, 1.2-inch×40-inch glass columns. The two columns were connected in series, side by side, and flushed with distilled water to remove contaminants. A 22 wt % aqueous solution (500 grams) of disodium methanedisulfonate (0.5 mole) was pumped at 25 mL per min through the first column (where most of the ion exchange occurs) and then through the second column to complete the conversion of the remaining salt. The feed was delivered in a downward mode followed by a 500 mL distilled water rinse. The combined solution was concentrated by distillation at atmospheric pressure to approximately 50% assay.

Example 51

Preparation of Methanetrisulfonic Acid—Preparation of Crude Methanetrisulfonic Acid—To a 1-liter, round-bottom flask under a nitrogen blanket was charged fuming sulfuric acid (30 wt %, 2.8 moles as $SO_3$, 750 grams). Acetic anhydride (0.55 moles, 56.6 grams) was added while letting the temperature rise to approximately 48° C. When all of the acetic anhydride was added, the reaction mixtures was heated slowly to approximately 100° C. and held there for approximately 19 hours to complete the reaction. The reaction mixture was cooled to approximately 20° C. and held for 1 hour. The reaction mixture was filtered on a glass frit and pulled under a plastic dam for 30 minutes to remove most of the sulfuric acid.

Preparation of Trisodium Methanetrisulfonate

The above solids (approximately 330 grams) were charged to deionized water, (770 grams) slowly while controlling the temperature below 70° C. After all solids dissolved, sodium hydroxide (50 wt %, approximately 411.9 grams) was added while letting the temperature rise to 50-60° C. and the pH rise to >12. The solution was held 30 minutes at 70° C., cooled to 40° C., seeded, and cooled slowly to 0-5° C. The cold slurry was held for 1 hour and filtered. The cake was washed with 250 mL deionized water at 0-5° C. The cake (578 grams) was recharged back to the 2-liter flask containing deionized water (750 grams). The slurry was heated to 58° C. while making a complete solution. The batch was then cooled to 40° C., seeded, cooled quickly to 0-5° C., and held for 1 hour at 0-5° C. The product was filtered on a Buchner funnel and the cake was washed with a cold 64% isopropyl alcohol and water mixture (150 grams). The wet cake was finally washed twice with isopropyl alcohol at ambient temperature. The batch was pulled down well under a plastic dam for 30 minutes. The product trisodium salt was dried in a 50° C., nitrogen-purged, vacuum oven (wet wt.=345 grams, dry wt.=208 grams). The dry solids were recharged back to a 2-liter, round-bottom flask with 750 grams deionized water. The batch was heated to approximately 60° C. to form a complete solution. To this solution was added 3 grams of DARCO™ G-60 activated carbon and the resulting mixture was held at 70° C. for 1 hour. The batch was clarified through a 1 micron fiberglass filter at 70° C. The water-white solution was then cooled to 40° C. and seeded. The solution began to crystallize at approximately 25° C. The crystallization mixture was held for 30 minutes at ambient temperature and then cooled to 0-5° C. for 1 hour. The white slurry was filtered on a Buchner funnel and the cake washed with a cold 64% isopropyl alcohol and water mixture (150 grams). The cake was washed again with isopropyl alcohol (75 grams) at ambient temperature. The batch was pulled down well under a plastic dam for 60 minutes. The product as the trisodium salt was dried in a 50° C., nitrogen-purged, vacuum oven (wet wt.=197.7 grams, theory=354.4 g, dry wt.=157.1 grams, wt. yield=44.3%, m.p.=139-142° C.). The water solubility of trisodium methanetrisulfonate is approximately 8.2%.

Preparation of Methanetrisulfonic Acid by Ion-Exchange

Water-wet, AMBERLYST-36™ ion-exchange resin (2000 grams) was charged to four, 2-inch×40-inch glass columns equipped with ground glass joints and TEFLON™ bottom stopcocks. The four columns are connected in series and flushed with deionized water to remove contaminants. An 8 wt % solution of methanetrisulfonic acid (1964 grams, 157.1 grams on a 100 wt % basis) was pumped at approximately 25 mL per minute through the first and second column (where most of the ion-exchange occurs), and then through the third and fourth column to complete the conversion of the remaining salt. The feed was pumped in a downward direction and followed by a 1000 mL deionized water rinse. The combined solution was concentrated at atmosphere pressure to approximately 50 wt % MTSA. The columns were regenerated using 1500 grams of a 10% sulfuric acid solution in the reverse flow mode. The columns were then flushed with deionized water to almost neutral pH and/or the pH of the starting water. The yield of MTSA was 124.9 grams, indicating approximately 100% conversion to MTSA.

Example 52

Preparation of Methylsulfonylmethanesulfonic Acid—Sodium methylsulfonylmethanesulfonate was prepared by the dropwise addition of 50 g (0.435 mole) of methanesulfonyl chloride to a solution of 61 g (0.65 mole) of triethylamine and 175 mL of acetonitrile over a period of about 0.5 hr at a temperature of −30 to −40° C. The resulting slurry was stirred for 45 minutes and then treated with 5 mL of water. The slurry was stirred 10 minutes, and the triethylamine hydrochloride was filtered off and washed with 75 mL of acetonitrile. The filtrate was stripped at room temperature at about 50 mm of pressure to an oil that was treated with 225 mL of 2N NaOH. The resulting solution was chilled in a refrigerator overnight and the sodium salt was recovered by filtration and washed with a little ice-water. After drying overnight in a vacuum oven at 80° C., 25.6 g of white solid was obtained (55% yield as the monohydrate, mp 235-240° C. with gas evolution). $H^1$NMR (DCl/$D_2O$): δ 3.2 (s, 3H); δ 5.0 (s, 2H).

Water-wet, AMBERLYST-36™ ion-exchange resin (1000 g, 55% solids, 5.4 meq/g, 5.4 eq), was charged to two, 2-inch× 40-inch glass columns equipped with ground glass joints and TEFLON™ bottom stopcocks. The two columns were connected in series and flushed with deionized water to remove contaminants. An 11% solution of sodium methanesulfonylmethanesulfonate in water (24 grams at 100% basis, 0.122 mole) was pumped at 25-40 mL per minute through the first column (where most of the ion-exchange occurs) and then through the second column to complete the conversion of the remaining salt. The feed was pumped in a downward mode and followed by a 500 mL deionized water rinse. The combined solutions were concentrated at reduced pressure to approximately 50 wt % solids. The columns were regenerated using 500 grams of a 10 wt % sulfuric acid solution in the reverse flow mode. The columns were then flushed with deionized water to an almost neutral pH for reuse. The product solution weighed 47 g and was analyzed by titration assay as 40.7 wt % product (89.9% assay yield). X-Ray analysis: Na 3 ppm; S 14.88% (theory 15.1%). Karl Fischer: $H_2O$ 59.7 wt %.

Example 53

Preparation of Bis(methylsulfonyl)methanesulfonic Acid—Phenyl methylsulfonylmethanesulfonate was prepared by adding methanesulfonyl chloride (112 g, 1 mole) dropwise to a solution of 210 mL (1.5 mole) of triethylamine and 400 mL of acetonitrile over a period of about 0.5 hr at −30° C. to −40° C. The resulting slurry was held for 45 min at −30° C. to −40° C. and treated with 47 g (0.5 mole) of phenol. The cooling bath (dry-ice:acetone) and the reaction flask were allowed to come to room temperature, and 600 mL of water and 100 mL of conc HCl were added. The acetonitrile was removed with vacuum at room temperature and the resulting solid was filtered and washed with water and air dried to give 86 g of crude solid that was recrystallized from 500 mL of methanol and 200 mL of water (0-5° C. filtration temperature). The yield of phenyl methylsulfonylmethanesulfonate was 74.5 g (59%); mp 175-176° C. $H^1$ NMR $CDCl_3$: δ 7.3-7.4 (m, 5H); δ 4.64 (s, 2H); δ 3.35 (s, 3H).

The above phenyl methylsulfonylmethanesulfonate (25 g, 0.1 mole) was dissolved in a solution of 75 mL of water and 8 g (0.1 mole) of 50% sodium hydroxide. The solution was cooled to 0-5° C. and treated with 11.4 g of methanesulfonyl chloride which was added dropwise over 45 min. The resulting slurry was filtered (starting material precipitates during the addition) and the solid (14.3 g after drying) was washed with 75 mL of water. The filtrate was treated with conc HCl until no more solid precipitated. The phenyl bis(methylsulfonyl)methanesulfonate product was filtered and washed with ice-water. After drying in a 60° C. vacuum oven the product (12.9 g, mp 154-156° C.) was recrystallized from ethyl acetate with a hot clarification to give 11.3 g, (34.4% conversion, 80% yield) of phenyl bis(methylsulfonyl)methanesulfonate as a white solid, mp 159-160° C. $H^1$NMR: δ 7.36-7.44 (m, 5H); δ 2.65 (s, 6H). No major impurities were detected by HPLC-MS.

A slurry of 11.2 g (34.1 mmole) of the above phenyl bis (methylsulfonyl)methanesulfonate and 40 mL of water were refluxed for 2 hr after which a complete solution was obtained. Thin layer chromatography (80 vol % acetone, 20 vol % heptane, with iodine visualization) indicated complete conversion to the desired product and phenol. The phenol was removed by extraction with 3×40 mL of ethyl acetate and the solution was evaporated at 50 mm pressure and 90° C. bath temperature to give 8.8 g (102% of theory) of bis(methylsulfonyl)methanesulfonic acid a white solid, mp>300° C. Titration analysis of the product gave 85 wt % bis(methylsulfonyl)methanesulfonic acid and Karl Fischer analysis showed 12 wt % water. $H^1$ NMR: δ 5.96 (s, 1H); δ 3.35 (s, 6H). No major impurities were detected by HPLC-MS.

Comparative Example 54

Rate of Hydrocarboxylation of Formaldehyde using $H_2SO_4$—$H_2SO_4$ (0.984 g, 0.010 mole) and water (5.04 g, 0.28 mole, includes water from HCHO and catalyst) were added to a 100 mL zirconium autoclave. To this solution was added HCHO (6.3 g, 95 wt %, 0.20 mole) and GA (30.4 g, 0.40 mole). The concentration of $H_2SO_4$ at the start of the reaction was 2.4 weight percent, based on the total weight of the starting reaction mixture. The system was purged with CO and pressurized to 17.2 bars gauge (250 psig) CO. The temperature in the autoclave was increased to 140° C. with stirring (1000 rpm). Upon reaching temperature, the pressure in the autoclave was increased to 69 bars gauge (1000 psig) CO. Once temperature and pressure were reached, the time 0 sample was taken. The pressure and temperature were maintained for 4 hours. Subsequent samples of the reaction were taken at approximately 30, 60, 90, 120, 150, 180, and 240 minutes. The yield of GA, the reaction rate, and weight percent of acid catalyst in the final product mixture are shown in Table 23.

Example 55

Rate of Hydrocarboxylation of Formaldehyde Using MTSA—The procedure of Example 54 was followed except that MTSA (1.24 g, 82 wt % assay, 0.004 mole) and water (4.5 g, 0.28 mole) were added to the zirconium autoclave. To this was added HCHO (6.3 g, 95 wt %, 0.20 mole) and GA (30.4 g, 0.40 mole). The concentration of MTSA at the start of the reaction was 2.4 weight percent, based on the total weight of the starting reaction mixture. The pressure and temperature were maintained for 4 hours and samples were taken at approximately 0, 30, 60, 90, 120, 150, 180, and 240 minutes. The yield of GA, the reaction rate, and weight percent of acid catalyst in the final product mixture are shown in Table 23.

Example 56

Rate of Hydrocarboxylation of Formaldehyde Using MDSA—The procedure of Example 54 was followed except that MDSA (1.94 g, 50 wt %, 0.006 mole) and water (3.84 g, 0.28 mole) were added to the zirconium autoclave. To this was added HCHO (6.3 g, 95 wt % assay, 0.20 mole) and GA (30.4 g, 0.40 mole). The concentration of MDSA at the start of the reaction was 2.4 weight percent, based on the total weight of the starting reaction mixture. The autoclave was secured to the stand and sealed. The system was purged with CO and pressurized to 17.2 bars gauge (250 psig) CO. The temperature in the autoclave was increased to 140° C. with stirring (1000 rpm). Upon reaching temperature, the pressure in the autoclave was increased to 69 bars gauge (1000 psig) CO. Once temperature and pressure were reached, a sample was taken which was designated as time 0. The pressure and temperature were maintained for 4 hours. Subsequent samples of the reaction were taken at approximately 30, 60, 90, 120, 150, 180, and 240 minutes. The yield of GA, the reaction rate, and weight percent of acid catalyst in the final product mixture are shown in Table 23.

Example 57

Rate of Hydrocarboxylation of Formaldehyde Using MMSA—The procedure of Example 54 was followed except that MMSA (2.56 g, 40.7 wt % assay, 0.006 mole) and water (0 g, total water is 0.1 mole from other starting materials) were added to the zirconium autoclave. To this was added HCHO (6.3 g, 95 wt % assay, 0.20 mole) and GA (40 g, 0.40 mole). The concentration of MMSA at the start of the reaction was 2.4 weight percent, based on the total weight of the starting reaction mixture. The pressure and temperature were maintained for 4 hours and samples were taken at approximately 0, 30, 60, 90, 120, 150, 180, and 240 minutes. The yield of GA, the reaction rate, and concentration of acid catalyst in the final product mixture are shown in Table 23.

Example 58

Rate of Hydrocarboxylation of Formaldehyde Using BMMSA—The procedure of Example 54 was followed except that BMMSA (1.19 g, 85 wt % assay, 0.004 mole) and water (4.53 g, 0.28 mole) were added to the zirconium autoclave. To this was added HCHO (6.3 g, 95 wt % assay, 0.20 mole) and GA (30.4 g, 0.40 mole). The concentration of BMMSA at the start of the reaction was 2.4 weight percent, based on the total weight of the starting reaction mixture. The pressure and temperature were maintained for 4 hours and samples were taken at approximately 0, 30, 60, 90, 120, 150, 180, and 240 minutes. The yield of GA, the reaction rate, and concentration of acid catalyst in the final product mixture are shown in Table 23.

The hydrocarboxylation experiments of Comparative Example 54 and Examples 55-58 shown in Table 23 illustrate the effect of the various sulfonated acids on the yield and rate of glycolic acid formation in comparison to the $H_2SO_4$-catalyzed reaction under the same reaction and sampling conditions. The data of Table 23 show higher yields and reaction rates for the MTSA-catalyzed reaction in comparison to the $H_2SO_4$-catalyzed process. The selectivity to glycolic acid was not reported for these experiments because competing reactions in the batch autoclave studies did not permit a representative calculation of selectivity.

TABLE 23

Relative Rate of Glycolic Acid Formation in Batch Reactions

| Example | Acid | Yield of GA (%) | Rate (mmol/g new GA) | Wt % Acid Cat. in Product Mixture |
|---|---|---|---|---|
| C-54 | $H_2SO_4$ | 15% | 1.0 | 1.6 |
| 55 | MTSA | 27% | 1.6 | 3.8 |
| 56 | MDSA | 18% | 1.0 | 2.7 |

TABLE 23-continued

Relative Rate of Glycolic Acid Formation in Batch Reactions

| Example | Acid | Yield of GA (%) | Rate (mmol/g new GA) | Wt % Acid Cat. in Product Mixture |
|---|---|---|---|---|
| 57 | MMSA | 16% | 1.0 | 2.7 |
| 58 | BMMSA | 9% | 0.6 | 4.0 |

Examples 59-61

Continuous Hydrocarboxylation of Formaldehyde to Glycolic Acid With MTSA—Examples 59-61 illustrate the effect of flow rate, temperature, pressure, and catalyst level on the hydrocarboxylation of formaldehyde with MTSA as the catalyst. The composition and flow rate of the feed to the reactor is given in Table 24. Overall feed molar flow ratios of GA relative to formaldehyde are presented in Table 25, along with reaction temperature, pressure, and residence time.

Conversion, space-time yield, and selectivity to end products based on reacted formaldehyde are shown in Table 26. As noted above, glycolic acid oligomers, esters, and other forms of glycolic acid were hydrolyzed to the corresponding acids prior to analysis by HPLC. Also, methanol that was present as methyl glycolate was converted to and reported as free methanol by the analytical method described above.

TABLE 24

Feed Rates and Composition for the Continuous Hydrocarboxylation of HFr

| | Feed | Feed Composition, wt % | | | |
|---|---|---|---|---|---|
| Example | g/min | Formaldehyde | water | GA | MTSA |
| 59 | 1.01 | 13.0 | 17.2 | 66.0 | 3.8 |
| 60 | 1.68 | 13.0 | 17.2 | 66.0 | 3.8 |
| 61 | 2.35 | 13.0 | 17.2 | 66.0 | 3.8 |

TABLE 25

Overall Feed Ratios and Reaction Conditions for the Continuous Hydrocarboxylation of HFr

| | Feed Molar Ratio | | | | Temperature (°C.) | Pressure (bars gauge) | Res Time (min) |
|---|---|---|---|---|---|---|---|
| Example | HFr | $H_2O$ | GA | MTSA | | | |
| 59 | 1.0 | 2.2 | 2.0 | 0.034 | 190 | 178.5 | 104 |
| 60 | 1.0 | 2.2 | 2.0 | 0.034 | 205 | 179.1 | 63 |
| 61 | 1.0 | 2.2 | 2.0 | 0.034 | 205 | 179.4 | 45 |

TABLE 26

Results for Continuous Hydrocarboxylation of HFr Using MTSA

| | % HFr Conv. | Molar Selectivity, % | | | | | Space-Time Yield (gmol/l-hr) | Wt % Acid Cat. in Prod. Mixture |
|---|---|---|---|---|---|---|---|---|
| Example | | GA | HOFr | DGA | MAA | MeOH | | |
| 59 | 93 | 87.8% | 4.7 | 2.1 | 1.7 | 3.8 | 2.0 | 3.5 |
| 60 | 94 | 89.2% | 3.0 | 4.0 | 1.7 | 2.2 | 3.5 | 3.5 |
| 61 | 93 | 88.5% | 3.5 | 3.5 | 2.0 | 2.4 | 4.8 | 3.5 |

Comparative Examples 62-67

Continuous Hydrocarboxylation of Formaldehyde to Glycolic Acid With $H_2SO_4$ Catalyst—Comparative Examples 62-67 illustrate the effect of feed flow rate, temperature, pressure, and catalyst level on the hydrocarboxylation of formaldehyde with sulfuric acid as the catalyst. For each example, a feed mixture with the composition shown in Table 27 was pumped to the reaction vessel. Overall feed molar flow ratios of water, GA, and sulfuric acid relative to HCHO are shown in Table 28, along with reaction temperature, pressure, and residence time. The feed mixture was prepared by mixing, water, $H_2SO_4$ and GA in a tank heated to 60° C. Paraformaldehyde was added with stirring until complete dissolution occurred. The feed was kept at 60° C. throughout the reaction period to ensure no solid formaldehyde precipitated.

Conversion, space-time yield, and selectivity to end products based on reacted formaldehyde are summarized in Table 29. Also, methanol that was present as methyl glycolate was converted to and reported as free methanol by the analytical method described above.

TABLE 27

Continuous Hydrocarboxylation of HFr with $H_2SO_4$ Catalyst - Rate and Composition of Feed

| Example | Feed rate (g/min) | Feed Composition, wt % | | | |
|---|---|---|---|---|---|
| | | HFr | $H_2O$ | GA | $H_2SO_4$ |
| C-62 | 1.00 | 13.0 | 17.2 | 66.0 | 3.8 |
| C-63 | 1.66 | 13.0 | 17.2 | 66.0 | 3.8 |
| C-64 | 2.33 | 13.0 | 17.2 | 66.0 | 3.8 |
| C-65 | 1.00 | 13.0 | 17.2 | 66.0 | 3.8 |
| C-66 | 1.66 | 13.0 | 17.2 | 66.0 | 3.8 |
| C-67 | 2.33 | 13.0 | 17.2 | 66.0 | 3.8 |

TABLE 28

Hydrocarboxylation of HFr with $H_2SO_4$ Catalyst - Overall Feed Ratios and Reaction Conditions

| Example | Feed Molar Ratio | | | | Temperature (° C.) | Pressure (bars gauge) | Res Time (min) |
|---|---|---|---|---|---|---|---|
| | HFr | $H_2O$ | GA | $H_2SO_4$ | | | |
| C-62 | 1.0 | 2.2 | 2.0 | 0.089 | 195 | 155.0 | 104 |
| C-63 | 1.0 | 2.2 | 2.0 | 0.089 | 205 | 179.5 | 63 |
| C-64 | 1.0 | 2.2 | 2.0 | 0.089 | 215 | 179.1 | 45 |
| C-65 | 1.0 | 2.2 | 2.0 | 0.089 | 210 | 179.5 | 104 |
| C-66 | 1.0 | 2.2 | 2.0 | 0.089 | 210 | 180.0 | 63 |
| C-67 | 1.0 | 2.2 | 2.0 | 0.089 | 210 | 179.3 | 45 |

TABLE 29

Results for Continuous Hydrocarboxylation of HFr Using $H_2SO_4$

| Example | % HFr Conversion | Molar Selectivity, % | | | | | Space-Time Yield (gmol/l-hr) | Wt % Acid Cat. in Prod. Mixture |
|---|---|---|---|---|---|---|---|---|
| | | GA | HOFr | DGA | MAA | MeOH | | |
| C-62 | 94 | 89.1 | 2.7 | 4.5 | 1.8 | 1.8 | 2.1 | 3.5 |
| C-63 | 93 | 89.2 | 2.9 | 4.1 | 1.7 | 2.0 | 3.6 | 3.5 |
| C-64 | 94 | 86.3 | 3.2 | 5.7 | 3.1 | 1.7 | 4.6 | 3.5 |
| C-65 | 96 | 85.2 | 2.9 | 7.3 | 3.3 | 1.2 | 1.9 | 3.4 |
| C-66 | 94 | 87.2 | 3.0 | 4.7 | 4.1 | 1.0 | 3.8 | 3.5 |
| C-67 | 93 | 86.2 | 3.7 | 4.0 | 4.8 | 1.4 | 5.0 | 3.5 |

We claim:

1. A process for the preparation of glycolic acid, comprising
    (A) contacting carbon monoxide with an aqueous formaldehyde reactant in the presence of an alkyl sulfonic acid catalyst containing from 1 to 5 carbon atoms to produce an aqueous glycolic acid mixture; and
    (B) recovering the alkyl sulfonic acid from the aqueous glycolic acid mixture by extracting the aqueous glycolic acid mixture with an extraction solvent comprising at least one tertiary amine, at least one onium carboxylate compound or a combination thereof; at least one modifier comprising an aliphatic carboxylic acid, an organophosphorus acid, or a combination thereof; and at least one diluent comprising carbon dioxide, an aliphatic hydrocarbon, a halogenated hydrocarbon, or a combination thereof to form an aqueous raffinate phase comprising a major amount of the glycolic acid contained in the aqueous glycolic acid mixture and an organic extract phase comprising a major amount of the acid catalyst contained in the aqueous glycolic acid mixture.

2. The process according to claim 1, wherein the molar ratio of carbon monoxide to formaldehyde is about 0.5:1 to about 100:1, and the contacting is at a pressure of about 35 to about 350 bars gauge and a temperature of about 160 to about 220° C.

3. The process according to claim 1, wherein the aqueous glycolic acid mixture comprises about 50 to about 95 weight percent glycolic acid and about 0.2 to about 12 weight percent of the alkyl sulfonic acid catalyst, each based on the total weight of the aqueous glycolic acid mixture.

4. The process according to claim 1, wherein the alkyl sulfonic acid catalyst comprises methanesulfonic acid, methanedisulfonic acid, methanetrisulfonic acid, bis(methylsulfonyl)methanesulfonic acid, methylsulfonylmethanesulfonic acid, or combinations thereof.

5. The process according to claim 1, wherein the alkyl sulfonic acid catalyst comprises methanesulfonic acid, methanedisulfonic acid, methanetrisulfonic acid, bis(methylsulfonyl)methanesulfonic acid, or combinations thereof.

6. The process according to claim 1, wherein the alkyl sulfonic acid catalyst comprises methanetrisulfonic acid.

7. The process according to claim 1, wherein the tertiary amine comprises tris(2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof.

8. The process according to claim 1 wherein the modifier comprises n-pentanoic acid, 2-methylbutanoic acid, 3-methylbutanoic acid, hexanoic acid, 2-ethylbutanoic acid, heptanoic acid, octanoic acid, 2-ethylhexanoic acid, pelargonic acid, nonanoic acid, decanoic acid, lauric acid, palmitic acid, bis(2-ethylhexyl)hydrogen phosphate, perfluorooctanoic acid, or a combination thereof.

9. The process according to claim 1 wherein the diluent comprises pentane, hexane, heptane, decane, methylcyclohexane, methylene chloride, chlorobenzene, dichlorobenzene, 1,2-dichloroethane, benzene, toluene, xylene, isoparaffinic mixed hydrocarbons having a boiling range between 90 and 325° C., or a combination thereof.

10. The process according to claim 1, further comprising
(C) separating the aqueous raffinate and organic extract phases; and
(D) extracting the organic extract phase from step (C) with an aqueous formaldehyde solution to form an aqueous formaldehyde extract comprising a major amount of the acid catalyst contained in the organic extract phase from step (C) and an organic raffinate phase comprising a minor amount of the acid catalyst contained in the organic extract phase.

11. The process according to claim 10 wherein the aqueous formaldehyde solution comprises about 35 to about 85 weight percent formaldehyde, based on the total weight of the aqueous formaldehyde solution, the aqueous formaldehyde extract comprises about 0.5 to about 10 weight percent, based on the total weight of the aqueous formaldehyde extract, of the alkyl sulfonic acid catalyst, and the weight ratio of the aqueous formaldehyde solution to the organic extract phase is about 0.1:1 to about 1:1.

12. The process according to claim 11 wherein the aqueous formaldehyde extract is recycled to step (A).

13. A process for the preparation of glycolic acid, comprising contacting carbon monoxide with a reaction mixture comprising an aqueous formaldehyde reactant and methanetrisulfonic acid to produce an aqueous glycolic acid mixture.

14. The process according to claim 13, wherein the molar ratio of carbon monoxide to formaldehyde is about 0.5:1 to about 100:1, the contacting is at a pressure of about 35 to about 350 bar gauge and a temperature of about 160 to about 220° C., and the concentration of methanetrisulfonic acid in the aqueous glycolic acid mixture is about 0.2 to about 12 weight percent.

15. A process for the preparation of glycolic acid, comprising
(A) contacting carbon monoxide with an aqueous formaldehyde reactant in the presence of an acid catalyst comprising methanesulfonic acid, methanedisulfonic acid, methanetrisulfonic acid, bis(methylsulfonyl)methanesulfonic acid, or a combination thereof to produce an aqueous glycolic acid mixture comprising about 70 to about 90 weight percent glycolic acid, based on the total weight of the aqueous glycolic acid mixture, and about 1 to about 10 weight percent of the acid catalyst;
(B) extracting the aqueous glycolic acid mixture with an extraction solvent, comprising
(i) about 5 to about 45 weight percent, based on the total weight of the extraction solvent, of a tertiary amine comprising tris(2-ethylhexyl)amine, tris(2-ethylbutyl)amine, trioctylamine, triisooctylamine, triisodecyl amine, tridodecylamine, tridecylamine, dioctyldecylamine, didecyloctylamine, or a combination thereof;
(ii) about 5 to about 45 weight percent, based on the total weight of the extraction solvent, of a modifier comprising 2-ethylhexanoic acid, lauric acid, bis(2-ethylhexyl)hydrogen phosphate, perfluorooctanoic acid, or a combination thereof, wherein the weight ratio of the modifier to the tertiary amine is about 1:1 to about 5:1; and
(iii) about 10 to about 90 weight percent of a diluent, based on the total weight of the extraction solvent, comprising hexane, heptane, decane, methylcyclohexane, benzene, toluene, xylene, isoparaffinic mixed hydrocarbons having a boiling range between 90 and 325° C., or a combination thereof;
to form an aqueous raffinate phase comprising a major amount of the glycolic acid contained in the aqueous glycolic acid mixture and an organic extract phase comprising a major amount of the acid catalyst contained in the aqueous glycolic acid mixture;
(C) separating the aqueous raffinate and organic extract phases; and
(D) extracting the organic extract phase from step (C) with an aqueous formaldehyde solution, comprising about 35 to about 85 weight percent formaldehyde, based on the total weight of the aqueous formaldehyde solution, to form an aqueous formaldehyde extract comprising a major amount of the acid catalyst contained in the organic extract phase from step (C) and an organic raffinate phase comprising a minor amount of the acid catalyst contained in the organic extract phase.

16. The process according to claim 15, further comprising
(E) contacting the aqueous raffinate phase from step (C) with a wash solvent comprising about 80 to about 100 weight percent, based on the total weight of the wash solvent, of a wash diluent comprising hexane, heptane, decane, methylcyclohexane, benzene, toluene, xylene, isoparaffinic mixed hydrocarbons having a boiling range between 90 and 325° C., or a combination thereof; and about 0 to about 20 weight percent of a wash modifier comprising 2-ethylhexanoic acid, lauric acid, bis(2-ethylhexyl)hydrogen phosphate, 2-ethylhexanol, 2-ethylbutanol, n-hexanol, n-octanol, n-decanol, or a combination thereof, to form a washed aqueous raffinate phase and an organic wash extract phase, wherein the weight ratio of the wash solvent to the aqueous raffinate phase is about 0.1:1 to about 1:1;
(F) separating the washed aqueous raffinate and organic wash extract phases; and
(G) combining the organic wash extract phase with the extraction solvent of step (B) or with the organic extract phase of step (C).

17. The process according to claim 15, wherein the acid catalyst comprises methanetrisulfonic acid.

18. The process according to claim 17, wherein the tertiary amine comprises tris(2-ethylhexyl)amine; the modifier comprises 2-ethylhexanoic acid; the diluent comprises hexane, heptane, decane, or a combination thereof; the wash solvent comprises hexane, heptane, decane, isoparaffinic mixed hydrocarbons having a boiling range between 90 and 325° C., or a combination thereof; the wash modifier comprises 2-ethylhexanoic acid, n-hexanol, n-decanol, or a combination thereof; and the weight ratio of the modifier to the tertiary amine is about 2:1 to about 4:1.

19. The process according to claim 15 wherein the aqueous formaldehyde solution of step (D) comprises about 40 to about 55 weight percent formaldehyde and the aqueous formaldehyde extract of step (D) is passed to step (A).

* * * * *